United States Patent
Mehta et al.

(10) Patent No.: US 11,471,269 B2
(45) Date of Patent: Oct. 18, 2022

(54) OPTICAL CYLINDER AND METHOD OF SURFACE TREATMENT OF THE SAME

(71) Applicants: SINGAPORE HEALTH SERVICES PTE LTD, Singapore (SG); NANYANG TECHNOLOGICAL UNIVERSITY, Singapore (SG)

(72) Inventors: Jodhbir Mehta, Singapore (SG); Andri Riau, Singapore (SG); Subramanian Venkatraman, Singapore (SG); Bo Liedberg, Singapore (SG); Debasish Mondal, Singapore (SG)

(73) Assignees: Singapore Health Services Pte Ltd, Singapore (SG); Nanyang Technological University, Singapore (SG)

(*) Notice: Subject to any disclaimer, the term of this patent is extended or adjusted under 35 U.S.C. 154(b) by 17 days.

(21) Appl. No.: 16/316,642

(22) PCT Filed: Jul. 26, 2017

(86) PCT No.: PCT/SG2017/050381
§ 371 (c)(1),
(2) Date: Jan. 10, 2019

(87) PCT Pub. No.: WO2018/021971
PCT Pub. Date: Feb. 1, 2018

(65) Prior Publication Data
US 2019/0151076 A1    May 23, 2019

(30) Foreign Application Priority Data
Jul. 26, 2016  (SG) .............................. 10201606175P

(51) Int. Cl.
*A61F 2/14*    (2006.01)
*A61L 27/32*   (2006.01)
(Continued)

(52) U.S. Cl.
CPC .............. *A61F 2/142* (2013.01); *A61L 27/16* (2013.01); *A61L 27/24* (2013.01); *A61L 27/32* (2013.01);
(Continued)

(58) Field of Classification Search
CPC .............................. A61K 31/785; A61F 2/142
See application file for complete search history.

(56) References Cited

U.S. PATENT DOCUMENTS 5,019,097 A * 5/1991 Knight ..................... A61F 2/14
  623/5.13
2004/0082996 A1  4/2004 Tsai et al.
(Continued)

FOREIGN PATENT DOCUMENTS

WO   WO-03/105725 A2   12/2003

OTHER PUBLICATIONS

Riau, A. K.; Mondal, D.; Yam, G. H., Setiawan, M.; Liedberg, B.; Venkatraman, S. S.; et al., Surface Modification of PMMA to Improve Adhesion to Corneal Substitutes in a Synthetic Core-Skirt Keratoprosthesis. ACS Applied Materials & Interfaces, Sep. 21, 2015, vol. 7, No. 39, pp. 21690-21702.
(Continued)

*Primary Examiner* — Dah-Wei D. Yuan
*Assistant Examiner* — Andrew J Bowman
(74) *Attorney, Agent, or Firm* — Marshall, Gerstein & Borun LLP

(57) ABSTRACT

Disclosed is an optical cylinder of a corneal prosthesis comprising: a) an optical cylinder comprising a solid polymer, and b) a plurality of nanoparticles forming a substantially uniform layer on a circumference of the solid polymer surface of the optical cylinder. Also disclosed are methods of surface treatment of optical cylinders of corneal prostheses, and corneal prostheses thereof.

8 Claims, 16 Drawing Sheets

(51) Int. Cl.
*A61L 27/16* (2006.01)
*A61L 27/24* (2006.01)

(52) U.S. Cl.
CPC ....... *A61L 2400/12* (2013.01); *A61L 2400/18* (2013.01); *A61L 2430/16* (2013.01)

(56) References Cited

U.S. PATENT DOCUMENTS

| | | | |
|---|---|---|---|
| 2005/0287111 A1* | 12/2005 | Schlenoff | A61L 29/085 424/78.3 |
| 2011/0212153 A1 | 9/2011 | Bellare et al. | |
| 2012/0071580 A1 | 3/2012 | Cho et al. | |

OTHER PUBLICATIONS

Riau, A. K. et al., Functionalization of the Polymeric Surface with Bioceramic Nanoparticles via a Novel, Nonthermal Dip Coating Method. Applied Materials & Interfaces, Dec. 1, 2016, vol. 8, No. 51, pp. 35565-35577.
Whitcher, J. P.; Srinivasan, M.; Upadhyay, M.P. Corneal blindness: a global perspective. Bull. World Health Organ. 2001, 38, 1625-1631.
Tan, D. T.; Dart, J. K.; Holland, E. J.; Kinoshita, S. Corneal transplantation. Lancet 2012, 379, 1749-1761.
Ilhan-Sarac, 0.; Akpek, E. K. Current concepts and techniques in keratoprosthesis. Curr. Opin. Ophthalmol. 2005, 16, 246-250.
Gomaa, A.; Comyn, 0.; Liu, C. Keratoprostheses in clinical practice—a review. Clin Exp Ophthalmol. 2010, 38, 211-224.
Garcia, J. P. Jr; de la Cruz, J.; Rosen, R. B.; Buxton, D. F. Imaging implanted keratoprostheses with anterior-segment optical coherence tomography and ultrasound biomicroscopy. Cornea 2008, 27, 180-188.
Turek SL. Physiology and mineralization of bone: In: Orthopeadics: principles and their applications. 4th ed. Philadelphia: J. B. Lippincott Company; 1984. p. 136-144.
Zheng, X.; Huang, M.; Ding, C. Bond strength of plasma-sprayed hydroxyapatite/Ti composite coatings. Biomaterials. 2000, 21, 841-849.
Stoch, A.; Brozek, A.; Kmita, G.; Stoch, J.; Jastrz, W. Electrophoretic coating of hydroxyapatite on titanium implants. J. Mol. Structure. 2001, 596, 191-200.
Lim, L. S. et al. Biological and Ultrastructural Properties of Acelagraft, a Freeze-Dried y-Irradiated Human Amniotic Membrane. Arch Ophthalmol 2010, 128(10): 1303-1310.
Shapses et al., "Osteopontin Facilitates Bone Resorption, Decreasing Bone Mineral Crystallinity and Content During Calcium Deficiency", Calcified Tissue Int., 73, 2003, pp. 86-92.
Pascolini et al., "Global Estimates of Visual Impairment: 2010", Br J Ophthalmol, 96, 2012, pp. 614-618.
J. Childress, "Ethical Criteria for Procuring and Distributing Organs for Transplantation", Journal of Health Politics, Policy and Law, vol. 14, No. 1, 1989, pp. 87-113.
Muraine et al., "Deep Lamellar Keratoplasty Combined With Cataract Surgery", Arch Ophthalmol, vol. 120, Jun. 2002, pp. 812-815.
Nouri et al., "Endophthalmitis After Keratoprosthesis; Incidence, Bacterial Causes, and Risk Factors", Arch Ophthalmol, vol. 119, Apr. 2001, pp. 484-489.
Wang et al., "Hydroxyapatite for Keratoprosthesis Biointegration", Investigative Ophthalmology & Visual Science, vol. 52, No. 10, Sep. 2011, pp. 7392-7399.
Salvador-Culla et al., "Titanium Coating of the Boston Keratoprosthesis", TVST, vol. 5, No. 2, Article 17, 2016, 12 pages.
Nieh et al., "Processing and Characterization of Hydroxyapatite Coatings on Titanium Produced by Magnetron Sputtering", J. Mater. Res., vol. 16, No. 11, Nov. 2001, pp. 3238-3245.
International Search Report and Written Opinion in International Application No. PCT/SG2017/050381 dated Oct. 2, 2017, 11 pages.
First Examination Report in IN Application No. 201817049745 dated Nov. 16, 2021, 6 pages.

* cited by examiner

|  | Ca | P | Ca/P |
|---|---|---|---|
| HAp NP | 63.3±1.5% | 36.7±1.5% | 1.73±0.11 |
| Dip + Plasma | 63.0±1.4% | 37.0±1.4% | 1.70±0.10 |

OPTICAL CYLINDER AND METHOD OF SURFACE TREATMENT OF THE SAME

CROSS-REFERENCE TO RELATED APPLICATIONS

This application claims the benefit of priority of Singapore provisional application No. 10201606175P, filed 26 Jul. 2016, the contents of it being hereby incorporated by reference in its entirety for all purposes.

FIELD OF THE INVENTION

The present invention generally relates to prostheses. In particular, the present invention relates to corneal implants and methods of treating the surface of said implants.

BACKGROUND OF THE INVENTION

Corneal disease is a leading cause of blindness worldwide, second only to cataract.[1] Globally, corneal disease is estimated to be responsible for blindness in 4.9 million individuals, which is equivalent to 12% of the total 39 million who are blind.[1,2] Currently, the only effective treatment for the disease is allogeneic corneal transplantation. However, donor corneal transplantation is often plagued with clinical, ethical and logistical limitations, such as global shortage of transplantation-grade corneas,[3] or the unavailability of infrastructure necessary for a transplantation service due to a lack of storage facilities, or cultural and religious issues.[4,5] The current surgical alternative to donor corneal transplantation is implantation of corneal prosthesis or in ophthalmic term, keratoprosthesis (KPro). The KPro design that is most widely used in the art is core-skirt KPro design that is illustrated in FIG. 1. A major challenge in preparing a core-skirt KPro is the fact that the surface properties of the core optic or the optical cylinder are often unfavorable for adhesion of the skirt (i.e. the human donor cornea). The weak adhesion of the skirt to the core optic or the optical cylinder can cause various problems such as epithelial downgrowth, bacterial infection, and leakage of aqueous humor. These problems may ultimately lead to device failure. In view of the above, there is a need to provide an alternative core optic or optical cylinder of a core-skirt KPro and an alternative method to treat the surface of said core optic or optical cylinder thereby allowing adhesion of the skirt to said core optic or optical cylinder.

SUMMARY OF THE INVENTION

In one aspect, there is provided an optical cylinder of a corneal prosthesis comprising: a) an optical cylinder comprising a solid polymer, and b) a plurality of nanoparticles forming a substantially uniform layer on a circumference of the solid polymer surface of the optical cylinder.

In one example, the solid polymer is optically transparent. In one example, the solid polymer is selected from the group consisting of poly(methyl methacrylate) (PMMA), polystyrene, polycarbonate, polythiourethane, polyethylene terephthalate, and polypropylene. In one example, the solid polymer is poly(methyl methacrylate) (PMMA).

In one example, the nanoparticle covers at least 70% of the circumference of the solid polymer surface of the optical cylinder. In one example, the Root Mean Square (RMS) roughness ($R_{RMS}$) value of the layer is from 150 nm to 80 nm. In one example, the thickness of the layer is from 30 μm to 100 μm.

In one example, the nanoparticle is insoluble in organic solvent. In one example, the nanoparticle is selected from the group consisting of bioceramic nanoparticle, metal nanoparticle, and a mixture thereof. In one example, the bioceramic nanoparticle is selected from the group consisting of hydroxyapatite (HAp) nanoparticle, titanium oxide ($TiO_2$) nanoparticle, aluminum oxide ($Al_2O_3$) nanoparticle, zirconium dioxide ($ZrO_2$) nanoparticle, and a mixture thereof. In one example, the bioceramic nanoparticle is hydroxyapatite (HAp) nanoparticle and/or titanium oxide ($TiO_2$) nanoparticle.

In one example, when the bioceramic nanoparticle is hydroxyapatite (HAp) nanoparticle, the Ca/P ratio of the layer is from 1.67 to 1.72.

In another aspect, there is provided a corneal prosthesis comprising an optical cylinder as disclosed herein.

In yet another aspect, there is provided a method of surface treatment of an optical cylinder of a corneal prosthesis, wherein the method comprises: a) contacting an optical cylinder comprising a solid polymer with a mixture comprising an organic solvent, a dispersant, and a plurality of nanoparticles to form a substantially uniform layer on a circumference of the solid polymer surface of the optical cylinder, and b) removing the organic solvent to immobilize the nanoparticle and the dispersant on the circumference of the solid polymer surface of the optical cylinder, thereby forming the optical cylinder of the corneal prosthesis.

In one example, the solid polymer is optically transparent. In one example, the solid polymer and the dispersant is selected from the group consisting of poly(methyl methacrylate) (PMMA), polystyrene, polycarbonate, polythiourethane, polyethylene terephthalate, and polypropylene. In one example, the solid polymer and the dispersant is poly(methyl methacrylate) (PMMA).

In one example, the contacting in a) is selected from a group of methods consisting of spray coating and dipcoating. In one example, the contacting in a) is dipcoating. In one example, the length of time for the contacting in a) is from 45 to 75 seconds. In one example, the length of time for the contacting in a) is about 60 seconds.

In one example, the removing in b) is selected from a group of methods consisting of evaporating and heating. In one example, the removing in b) is evaporating.

In one example, the concentration of the nanoparticle in the mixture is from 15% (w/v) to 25% (w/v). In one example, the concentration of the nanoparticle in the mixture is about 20% (w/v).

In one example, the concentration of the dispersant in the mixture is from 4% (w/v) to 6% (w/v). In one example, the concentration of the dispersant in the mixture is about 5% (w/v).

In one example, the organic solvent is selected from the group consisting of chloroform ($CHCl_3$), dichloromethane ($CH_2Cl_2$), acetone, toluene, tetrahydrofuran (THF), dimethylformamide (DMF), tetrachloromethane (carbon tetrachloride), 1,4-dioxane, xylene, cyclohexanone, ethyl acetate, and diethyl carbonate. In one example, the organic solvent is chloroform ($CHCl_3$).

In one example, the nanoparticle is insoluble in organic solvent. In one example, the nanoparticle is selected from the group consisting of bioceramic nanoparticle, metal nanoparticle, and a mixture thereof. In one example, the bioceramic nanoparticle is selected from the group consisting of hydroxyapatite (HAp) nanoparticle, titanium oxide ($TiO_2$) nanoparticle, aluminum oxide ($Al_2O_3$) nanoparticle, zirconium dioxide ($ZrO_2$) nanoparticle, and a mixture thereof. In one example, the bioceramic nanoparticle is hydroxyapatite (HAp) nanoparticle and/or titanium oxide ($TiO_2$) nanoparticle. In one example, the size of the nanoparticle is from 20 nm to 100 nm. In one example, when the bioceramic nanoparticle is hydroxyapatite (HAp) nanoparticle, the size of the bioceramic nanoparticle is about 60 nm. In one example, when the bioceramic nanoparticle is titanium oxide ($TiO_2$) nanoparticle, the size of the bioceramic nanoparticle is about 50 nm.

In one example, the method further comprises exposing the layer to a plasma treatment.

In yet another aspect, there is provided an optical cylinder of a corneal prosthesis obtainable by the method disclosed herein.

In yet another aspect, there is provided a corneal prosthesis comprising an optical cylinder as disclosed herein.

BRIEF DESCRIPTION OF THE DRAWINGS

The invention will be better understood with reference to the detailed description when considered in conjunction with the non-limiting examples and the accompanying drawings, in which:

FIG. 1 describes an example of the optical cylinder as described herein.

FIG. 2A shows a macroscopic photograph and a Scanning Electron Microscopy (SEM) result depicting delamination of CaP coating on the taped half of the PMMA sheet. FIG. 2B shows an Atomic Force Microscopy (AFM) result depicting patchy and aggregates of the poly-dopamine layer on PMMA. The non-homogenous and irregular dopamine coating on PMMA depicted herein might contribute to the weak attachment of the CaP coating. FIG. 2C shows an Energy-dispersive X-ray spectroscopy (EDX) result depicting low Ca/P ratio of SBF-assembled CaP coating, which might partly contribute to the weak coating attachment. FIG. 2D shows a graphical illustration depicting combination of non-homogenous poly-dopamine layer and desorption of the CaP layers led to reduced adhesion of collagen on d-CaP surface. Thus, FIG. 2 illustrates that known method in the art does not provide homogeneous coating layer which then leads to poor coating retention.

FIG. 3A shows a Scanning Electron Microscopy (SEM) result depicting coating outcomes on PMMA surfaces when HAp nanoparticles were added in organic solvent (shown here in chloroform) without addition of 5% PMMA in dip coating solution. SEM result showed that clumps of nanoparticles were formed on the surface during the dip coating process regardless of the length of the dip coating time. FIG. 3B shows a graphical illustration depicting a rapid agglomeration rate of HAp nanoparticles in the chloroform without addition of 5% PMMA, leading to the formation of clumps of HAp upon settling on the PMMA surface. FIG. 3C shows a pair of photographs depicting dispersion of nanoparticles in organic solvent (shown here in chloroform) with and without 5% (w/v) PMMA. After 30 minutes, most HAp nanoparticles had agglomerated and settled at the bottom of the glass vial containing chloroform without 5% PMMA. In contrast, the nanoparticles were still well dispersed in the solution with 5% PMMA. FIG. 3D shows a bar graph depicting result of nanozetasizer measurement which revealed a significantly higher polydispersity index (PdI) of the nanoparticles in the solution without PMMA than that containing PMMA. *$p<0.05$. Thus, FIG. 3 illustrates that addition of dispersant such as 5% (w/v) PMMA to the dipcoating mixture reduces the agglomeration propensity or the clumping of the nanoparticles thereby providing ample time for the dispersed nanoparticles to be laid on the surface of the solid polymer in a more uniform and homogenous fashion.

FIG. 4A shows a Scanning Electron Microscopy (SEM) result and a graphical illustration depicting that organic solvent (e.g. chloroform) in the dipcoating solution 'softened' the surface of the PMMA substrate, creating cavities. FIG. 4B shows a Scanning Electron Microscopy (SEM) result and a graphical illustration depicting that the addition of lower concentration of nanoparticles demonstrated that nanoparticles could be trapped and immobilized in the cavities. The black arrows indicated nanoparticles that settled at the bottom of a cavity. In some areas, cavities were completely populated by nanoparticles, for example the area indicated by the white arrows. FIG. 4C shows a Scanning Electron Microscopy (SEM) result and a graphical illustration depicting that by doubling the concentration of the nanoparticles in the dip coating solution, the craters were completely populated by the nanoparticles. The entire PMMA surface appeared to be covered by layers of HAp. Thus, FIG. 4 demonstrates that higher concentration of nanoparticles in the dipcoating mixture allows for formation of thicker and more compact nanoparticles layer due to the tendency of nanoparticles to aggregate.

FIG. 5A shows a pair of Scanning Electron Microscopy (SEM) results depicting that plasma treatment removed residual contaminants from the surface that masked the HAp and in the process, revealed more HAp nanoparticles on the surface. Macroscopic view of the HAp-coated PMMA showed uniform and homogenous surface distribution of the HAp. FIG. 5B shows an Atomic Force Microscopy (AFM) result and a line graph depicting a relatively smoother surface after plasma treatment and confirming the SEM observation on FIG. 5A. Representative lateral roughness profile was extracted from the black line indicated on the AFM image. FIG. 5C shows an Attenuated Total Reflectance-Fourier Transform Infrared Spectroscopy (ATR-FTIR) result depicting that the weaker peaks of PMMA after plasma treatment. The surface now resembled more closely to the IR profile of pure HAp. FIG. 5D shows Energy-dispersive X-ray spectroscopy (EDX) result depicting Similar Ca/P composition of HAp nano-powder and plasma treated HAp-coated PMMA ($p=0.688$). FIG. 5E shows a macroscopic photograph and a Scanning Electron Microscopy (SEM) result depicting result of tape adhesion test (delamination test) that demonstrated that the HAp coated was intact and could not be easily delaminated from the PMMA. Thus, FIG. 5 shows that plasma treatment exposes nanoparticles and increases the relative smoothness of the nanoparticles surface without reducing the strength of the nanoparticles attachment to the solid polymer.

FIG. 6 illustrates that the surface of nanoparticles-coated solid polymer and the surface of plasma treated, nanoparticles-coated solid polymer is more hydrophilic when compared to the untreated solid polymer.

FIG. 8 illustrates that the nanoparticles do not penetrate deep into the solid polymer thereby allowing light to penetrate through the part of the solid polymer that is not covered by the nanoparticles.

FIG. 10A shows a bar graph depicting the shear adhesion strength test results of collagen on HAp-coated PMMA, untreated PMMA and CaP-coated PMMA via SBF incubation (d-CaP). Height of error bars indicates standard deviation of means. *$p<0.001$ relative to untreated PMMA group. FIG. 10B shows a graphical illustration depicting the HAp nanoparticles acting as an intermediate layer that interlocks PMMA and collagen. This interlocking mechanism improves the shear adhesion strength of collagen on PMMA. Thus, FIG. 10 illustrates that because the nanoparticles interlock the solid polymer to collagen (i.e. a type of protein that is abundant in corneal tissue), the shear adhesion strength of the nanoparticles-coated solid polymer is higher than the prior art (i.e. CaP-coated PMMA).

FIG. 11A shows a Scanning Electron Microscopy (SEM) result depicting the immobilized $TiO_2$ nanoparticles on PMMA substrate at low magnification (5,000×). FIG. 11B shows a Scanning Electron Microscopy (SEM) result depicting the immobilized $TiO_2$ nanoparticles on PMMA substrate at high magnification (15,000×). Thus, FIG. 11 demonstrates that other types of nanoparticles can be employed for the surface treatment method disclosed herein.

FIG. 12A shows a Scanning Electron Microscopy (SEM) result depicting the craters or voids created on PMMA substrate after being dipcoated in 5% PMMA/chloroform without HAp nanoparticles. FIG. 12B shows a Scanning Electron Microscopy (SEM) result depicting trapped HAp nanoparticles in the craters after 15 seconds of dipcoating in the mixture of 20% (w/v) nanoparticles in 5% PMMA/chloroform. FIG. 12C and FIG. 12D respectively show a low magnification and a high magnification of Scanning Electron Microscopy (SEM) results depicting layers of HAp covering the surface of PMMA after 1 min of dipcoating. FIG. 12E shows a photograph depicting the macroscopic appearance of the coated PMMA substrate after 1 min of dipcoating. Thus, FIG. 12 demonstrates that longer dipcoating time allows for formation of thicker and more compact nanoparticles layer due to the tendency of nanoparticles to aggregate.

DETAILED DESCRIPTION OF THE PRESENT INVENTION

Figure 1:
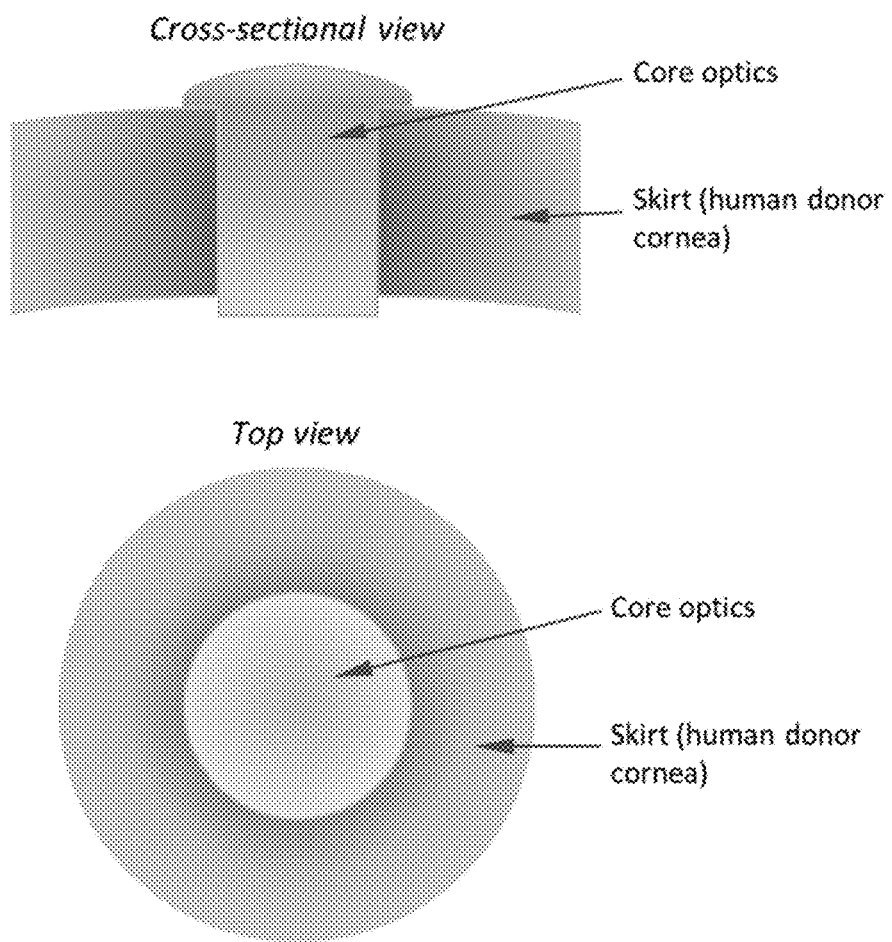
FIG. 1 shows a graphical illustration depicting main components of a core-skirt Keratoprosthesis (KPro). In this KPro design, the core optical cylinder is made of poly (methyl methacrylate) (PMMA) and is surrounded by skirt material, which conventionally is a human donor cornea.

There are many KPros that have been used clinically with varying surgical complexity and success rate, however the core-skirt KPro is the most widely used design. In the core-skirt design concept, solid polymer such as poly(methyl methacrylate) (PMMA) is used as primary material of the optical axis of the KPro. The solid polymer serves as the optical core to the surrounding donor corneal tissue (see illustrations in FIG. 1). The core-skirt constructional design has been shown to be one of the most successful designs, whereby the solid polymer provides resistance to biodegradability of the device, and the surrounding corneal tissue allows for host tissue integration. However, due to the surface properties of solid polymer that are generally unfavorable for tissue/cell adhesion, it has been a challenge to improve the skirt material-solid polymer integration. The combination of perpetual eyeball movement and blinking, and poor adhesion between solid polymer and the surrounding tissue inevitably detaches the corneal tissue from the solid polymer surface, allowing the possibility of epithelial downgrowth, bacterial infection, leakage of aqueous humor, and possibly leading to device failure. In addition, the incompatibility of solid polymer with corneal stromal fibroblasts further substantiate the need to improve the design of the core-skirt KPro.

Surface modification of the solid polymer is a technique that can be employed to improve the bonding between the two dissimilar materials and to support biointegration without significantly altering the bulk properties of both materials. Therefore, the clinical advantage of applying surface modification in addressing this problem is an improved performance of the device without the need to change the primary components and design of the original KPro. Developing a medical device with new biomaterials can be a tedious process that would take more than a decade to reach the clinical trial stage.

There is currently no surface coating technology that has been commercially applied on KPro optical cylinder (such as PMMA optical cylinder). There have only been a few published study that have attempted to surface modify the solid polymer cylinder with an aim to improve its adhesion to corneal tissue. One of the study attempted to coat the surface of the PMMA, which had been pre-treated with dopamine and 11-mercaptoundecanoic acid (11-MUA), with hydroxyapatite (HAp) by incubation of the polymer in 1.5× simulated body fluid (SBF) for 14 days. Using in vitro mechanical testing, the authors showed that the force required to detach the corneal tissue from the HAp-coated PMMA was increased by an order of magnitude compared to non-coated PMMA. HAp, a bioactive ceramic, was also shown to be biocompatible to corneal stromal fibroblasts and promote cell adhesion.

Figure 2:
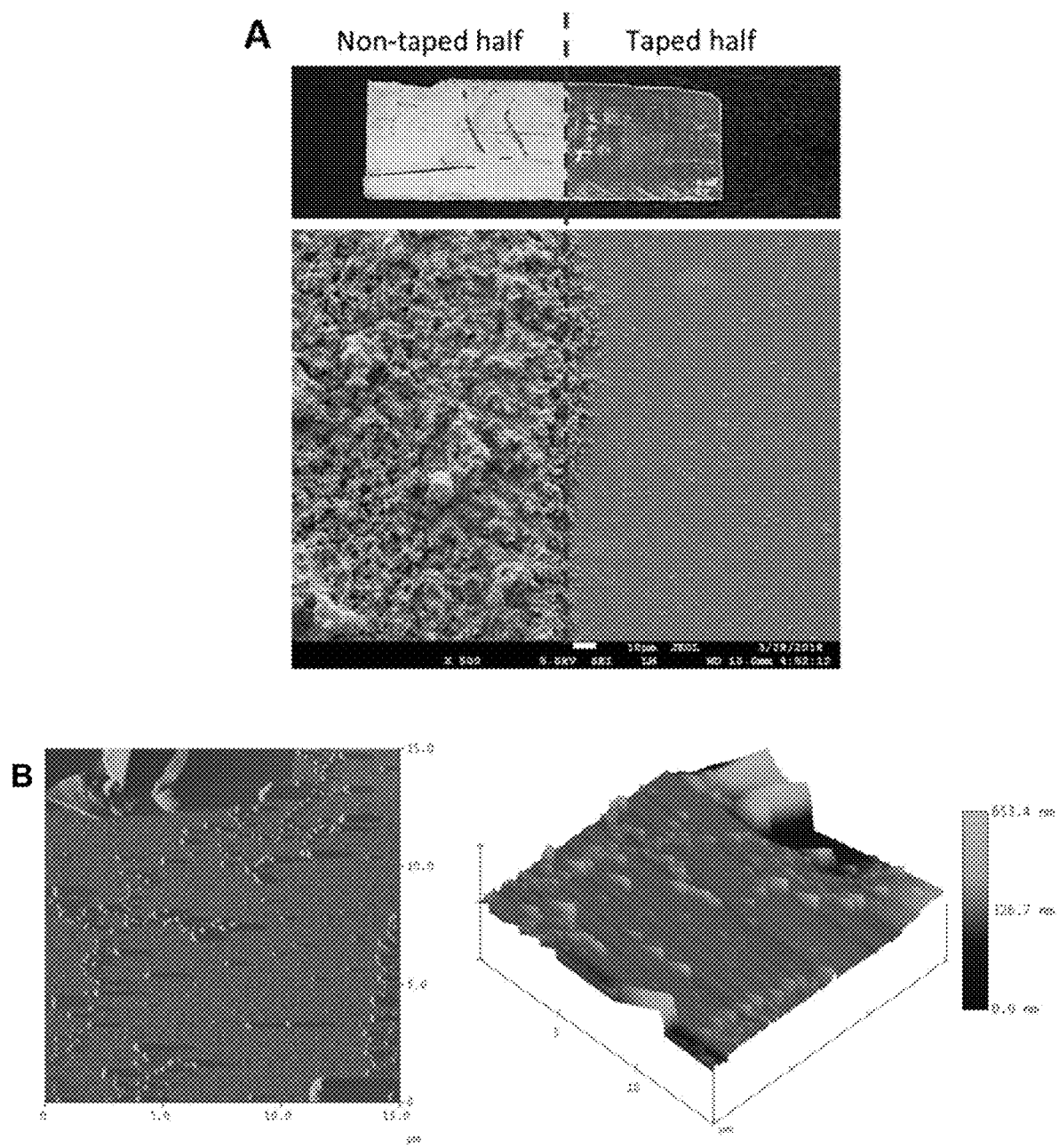
FIG. 2 shows data obtained from delamination test of (Calcium Phosphate) CaP coating produced by incubation in Simulated Body Fluid (SBF).
Figure 2:
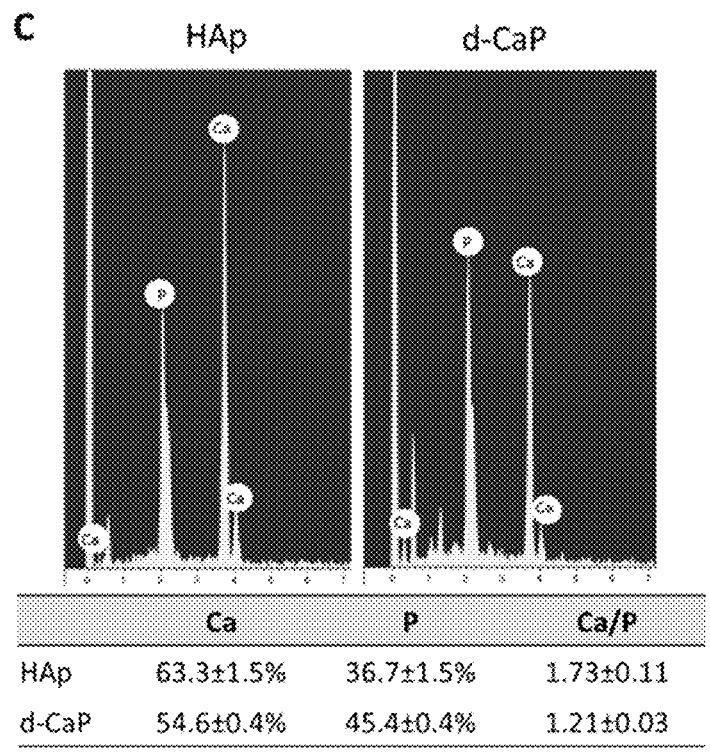
Figure 2:
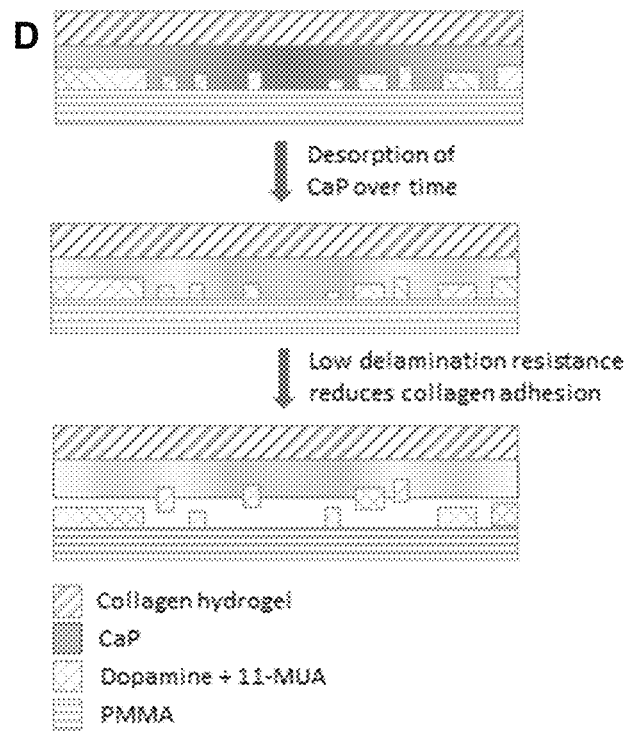

Although the study have shown that incubation in SBF leads to formation of bone-like apatite on PMMA surface, the resulting CaP coating did not attach well on dopamine activated PMMA surface and did not exhibit intrinsic properties of hydroxyapatite (HAp). In previous study, it was shown that the CaP coating was lifted together with the collagen hydrogel following the shear adhesion test, suggesting a better bonding between the collagen and CaP than between the CaP and dopamine-activated PMMA. Furthermore, as illustrated on FIG. 2, the underlying dopamine and 11-MUA (laid before CaP deposition) did not form a homogenous coating layer, which causes the CaP layer to have weak anchorage on the PMMA surface and thus reducing the adhesion of collagen on the CaP-coated PMMA.

In view of the above problems, there is a need to provide an alternative optical cylinder of a corneal prosthesis and an alternative method to treat the surface of the optical cylinder to allow for the adhesion of collagen (i.e. a type of protein that is abundant in corneal tissue that forms the skirt of a core-skirt KPro) to said optical cylinder.

The inventors of the present disclosure have found an alternative optical cylinder of a corneal prosthesis and an alternative method to treat the surface of the optical cylinder. Thus, in one aspect the present disclosure provides an optical cylinder of a corneal prosthesis comprising: a) an optical cylinder comprising a solid polymer, and b) a plurality of nanoparticles forming a substantially uniform layer on a circumference of the solid polymer surface of the optical cylinder.

As used herein, the term "corneal prosthesis" may refer to keratoprosthesis (KPro), which is an object that is implanted in the eye and acts as an artificial cornea. There are various types of keratoprostheses. In one example, the keratoprosthesis may be a core-skirt KPro. As illustrated on FIG. 1, in one example, the core-skirt KPro may comprise at least one core optic and a skirt. The skirt of a core-skirt KPro is located around and is bonded on the core optic. In one example, the skirt of a core-skirt KPro may comprise cornea or human donor cornea. The core optic of a core-skirt KPro typically has a cylindrical shape and thus may be referred as "optical cylinder". Therefore, as used herein, the term "optical cylinder" refers to a cylindrical object that is incorporated within the eye or the cornea or part thereof. In one example, the optical cylinder comprises a solid polymer. In one example, the optical cylinder is a solid polymer. As used herein, the term "solid polymer" refers to a polymer which is firm and stable in shape and is not liquid or fluid. As used herein, the term "polymer" refers to a large molecule, or macromolecule, composed of many repeated subunits that are termed as "monomers". In some examples, the polymer may contain one type of monomer and is therefore referred as "homopolymer". In some examples, the polymer may contain more than one type of monomer and therefore is referred as "heteropolymer". The term "polymer" may also refer to a plurality of large molecules, or plurality of macromolecules, composed of many repeated subunits.

As the solid polymer is to be used as a part of corneal prosthesis, in one example, the solid polymer is optically transparent. As used herein, the term "optically transparent" refers to the physical property of allowing light to pass through the material without being scattered. Light is capable of passing through the bulk of an optically transparent solid polymer that is not covered by the nanoparticles layer. In some examples, the solid polymer may include, but is not limited to, poly(methyl methacrylate) (PMMA), polystyrene, polycarbonate, polythiourethane, polyethylene terephthalate, polypropylene, and the like. In one example, the solid polymer is poly(methyl methacrylate) (PMMA).

In the present disclosure, a plurality of nanoparticles forms a substantially uniform layer on a circumference of the solid polymer surface of the optical cylinder. An exemplary illustration of this uniformity can be found on FIG. 7. As used herein, the term "substantially uniform" refers to the quality of an object wherein for the most part, the object has the same characteristic. Without wishing to be bound by theory, substantial uniformity of the nanoparticle layer plays a role in providing good coating retention which therefore allows the optical cylinder to remain bonded or adhered to the surrounding corneal tissue. The substantial uniformity of the nanoparticle layer may also provide additional contact points between the corneal tissue (such as the collagen or the collagen of the corneal tissue) that may improve the adhesion between the nanoparticle layer and the corneal tissue. The substantial uniformity of the nanoparticle layer can be determined using various types of measurements known in the art. The nanoparticle layer disclosed herein is substantially uniform because substantial part of the layer may have similar thickness, or similar roughness (such as similar $R_{RMS}$ value), or similar chemical composition (such as similar Ca/P value).

As used herein, the term "nanoparticles" or "nanoparticle" refers to an object having the size from 1 nm to 300 nm that behaves as a whole unit with respect to its transport and properties. Because the nanoparticles are part of a corneal prosthesis, the nanoparticles have to be biocompatible (i.e. not harmful and nontoxic to living cells and living tissue). In one example, the nanoparticle is insoluble in organic solvent. In some examples, the nanoparticle may include, but is not limited to, bioceramic nanoparticle, metal nanoparticle, and a mixture thereof. As used herein, the term "bioceramic" refers to biocompatible ceramic. The nanoparticle is intended as a permanent structure. An example of the permanent structure is a substantially uniform layer that coats the circumference of the solid polymer surface of the optical cylinder and thus allows the optical cylinder to adhere to the cornea. In some examples, the bioceramic nanoparticle may include, but is not limited to, hydroxyapatite (HAp) nanoparticle, titanium oxide ($TiO_2$) nanoparticle, aluminum oxide ($Al_2O_3$) nanoparticle, zirconium dioxide ($ZrO_2$) nanoparticle, and a mixture thereof. In some examples, the metal nanoparticle may include, but is not limited to, gold nanoparticle, silver nanoparticle, and a mixture thereof. The term "a mixture of nanoparticles" as used herein refers to a plurality of nanoparticles that contain more than one type of nanoparticle. Thus, in one example, the bioceramic nanoparticle may be a mixture of hydroxyapatite (HAp) nanoparticle and titanium oxide ($TiO_2$) nanoparticle. In one example, the bioceramic nanoparticle may be hydroxyapatite (HAp) nanoparticle. In one example, the bioceramic nanoparticle may be titanium oxide ($TiO_2$) nanoparticle.

Figure 7:
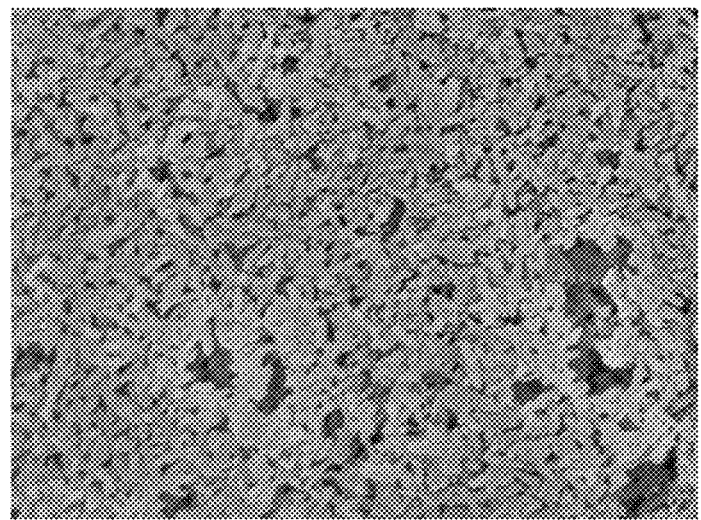
FIG. 7 shows a high magnification Scanning Electron Microscopy (SEM) result and a post-processed image thereof depicting good coverage and nanoparticles distribution on the plasma treated dipcoated PMMA surface. Bottom pane: Post-processed image from the upper pane (using ImageJ) revealed 77±5% nanoparticles coverage on the surface. Value was obtained by averaging 60 images (20 from each sample; n=3) taken from different areas throughout the surface of the substrate. Thus, FIG. 7 demonstrates that substantially uniform layer of nanoparticles is formed on the surface of the solid polymer.
Figure 7:
Figure 7:
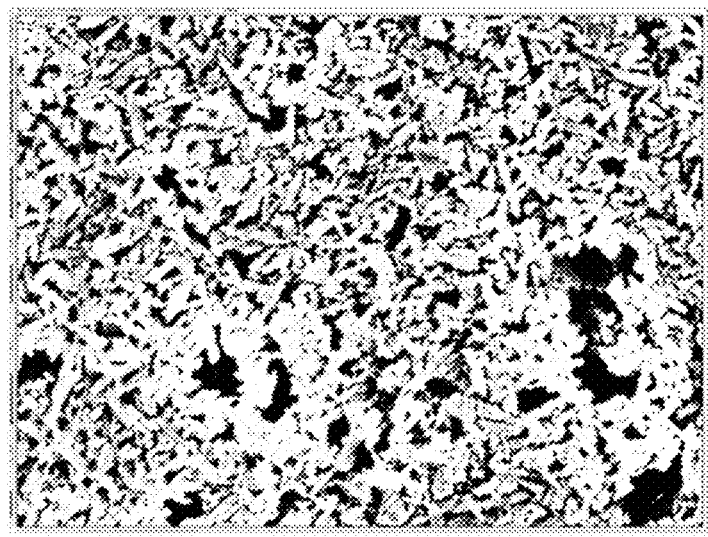

As disclosed above, the inventors of the present disclosure surprisingly found that the nanoparticle layer substantially covers the circumference of the solid polymer surface of the optical cylinder. Thus, in some examples, the nanoparticle covers at least 70%, or at least 75%, or at least 80%, or at least 85%, or at least 90%, or at least 95%, or at least 97.5%, or at least 99%, or at least 99.5%, or at least 99.9%, or 100% of the circumference of the solid polymer surface of the optical cylinder. In one example, the nanoparticle covers at least 70% of the circumference of the solid polymer surface of the optical cylinder. For example, FIG. 7 shows that 77±5% of the solid polymer surface was populated by the nanoparticles.

Additionally, the inventors of the present disclosure surprisingly found that the layer formed by the nanoparticles is relatively smooth. The roughness of the layer can be quantitatively measured or qualitatively observed using any method known in the art. In one example, qualitative observation of surface roughness may be performed using Scanning Electron Microscope (SEM). In one example, quantitative measurement of surface roughness may be performed using Atomic-Force Microscope (AFM). The result of a quantitative observation of surface roughness can be represented as "Root Mean Square (RMS) roughness" or "$R_{RMS}$" value. As used herein, the term "Root Mean Square (RMS) roughness" or "$R_{RMS}$" value refers to a measurement that is commonly used in the art to evaluate and describe the roughness of a surface. The "Root Mean Square (RMS) roughness" or "$R_{RMS}$" value is given by the standard deviation of the z-values for the sample area. It is generally known in the art that lower $R_{RMS}$ value signify a smoother surface.

The layer formed by the nanoparticles is relatively smooth because in some examples, the Root Mean Square (RMS) roughness ($R_{RMS}$) value of the layer is from 250 nm to 80 nm, or from 240 nm to 80 nm, or from 230 nm to 80 nm, or from 220 nm to 80 nm, or from 210 nm to 80 nm, or from 200 nm to 80 nm, or from 190 nm to 80 nm, or from 180 nm to 80 nm, or from 170 nm to 80 nm, or from 160 nm to 80 nm, or from 150 nm to 80 nm, or from 140 nm to 80 nm, or from 130 nm to 80 nm, or from 120 nm to 80 nm, or about 250 nm, or about 240 nm, or about 230 nm, or about 220 nm, or about 210 nm, or about 200 nm, or about 190 nm, or about 180 nm, or about 170 nm, or about 160 nm, or about 150 nm, or about 140 nm, or about 130 nm, or about 120 nm, or about 110 nm, or about 100 nm, or about 90 nm, or about 80 nm. In one example, the Root Mean Square (RMS) roughness ($R_{RMS}$) value of the layer is from 150 nm to 80 nm. For example, Table 1 shows that the surface roughness (i.e. the $R_{RMS}$) of the nanoparticles layer is 102.2±14.4.

The inventors of the present disclosure also surprisingly found that the nanoparticles on the surface of the solid polymer form a thin layer on the circumference of the solid polymer surface of the optical cylinder. The thickness of the (nanoparticles) layer can be measured using any method known in the art. In one example, the measurement of (nanoparticles) layer thickness may be performed by using Scanning Electron Microscope (SEM). The Scanning Electron Microscope (SEM) may be used to obtain a cross-sectional image (i.e. an image taken at right angles to an axis such as the axis of the optical cylinder) and the measurement of (nanoparticles) layer thickness may be obtained by specifically measuring the part of the cross-sectional image that corresponds to the nanoparticle layer. Formation of a thin nanoparticles layer may signify that the nanoparticles had not penetrated deeper into the solid polymer, thus the risk of visual obstruction to the patient who has the optical cylinder as prosthesis is not increased. As exemplified on FIG. 8, because the layer formed is thin and the nanoparticles do not penetrate deep into the solid polymer of the optical cylinder, the part of the optical cylinder that is not covered by the nanoparticle layer remains optically transparent.

In view of the above, in some examples, the thickness of the (nanoparticles) layer is from 5 μm to 100 μm, or from 10 μm to 90 μm, or from 15 μm to 80 μm, or from 20 μm to 70 μm, or from 25 μm to 60 μm, or from 30 μm to 50 μm, or from 5 μm to 20 μm, or from 20 μm to 40 μm, or from 40 μm to 60 μm, or from 60 μm to 80 μm, or from 80 μm to 100 μm, or about 30 μm, or about 31 μm, or about 32 μm, or about 33 μm, or about 34 μm, or about 35 μm, or about 36 μm, or about 37 μm, or about 38 μm, or about 39 μm, or about 40 μm, or about 41 μm, or about 42 μm, or about 43 μm, or about 44 μm, or about 45 μm, or about 46 μm, or about 47 μm, or about 48 μm, or about 49 μm, or about 50 μm. In some examples, the thickness of the (nanoparticles) layer is from 30 μm to 50 μm or from 30 μm to 100 μm. In one example, the thickness of the (nanoparticles) layer is from 30 μm to 100 μm.

Further to the above, the inventors of the present disclosure surprisingly found that the chemical composition of the layer formed from the nanoparticles closely resembles the chemical composition of the nano-powder itself. The term "nano-powder" as used herein refers to solid powders of nanoparticles. In one example, the layer is formed from the nano-powder. The chemical composition of the layer or the nano-powder can be determined with any method or any instrument known in the art. In one example, when the layer is formed from bioceramic nanoparticles, the chemical composition may be determined as Ca/P ratio. As used herein, the term "Ca/P ratio" refers to the atomic ratio of elemental calcium and phosphorus in a material. The detection of elemental calcium and phosphorus in a material and the determination of Ca/P ratio can be performed using any instruments and/or methods known in the art. In one example, the determination of Ca/P ratio may be performed by Energy-dispersive X-ray spectroscopy. In some examples, when the hydroxyapatite (HAp) nanoparticle layer is formed from the hydroxyapatite (HAp) nano-powder, the Ca/P ratio of the hydroxyapatite (HAp) nano-powder is measured before the formation of the nanoparticle layer, after the formation of the nanoparticle layer, and/or after the plasma treatment on the nanoparticle layer. Without wishing to be bound by theory, it is believed that calcium deficient nano-powder and calcium deficient nanoparticle layer (i.e. nano-powder and nanoparticle layer having Ca/P ratio of less than 1.67) may be less resistant to biodegradation (i.e. the process by which substances are decomposed into simpler substances).

Figure 5:
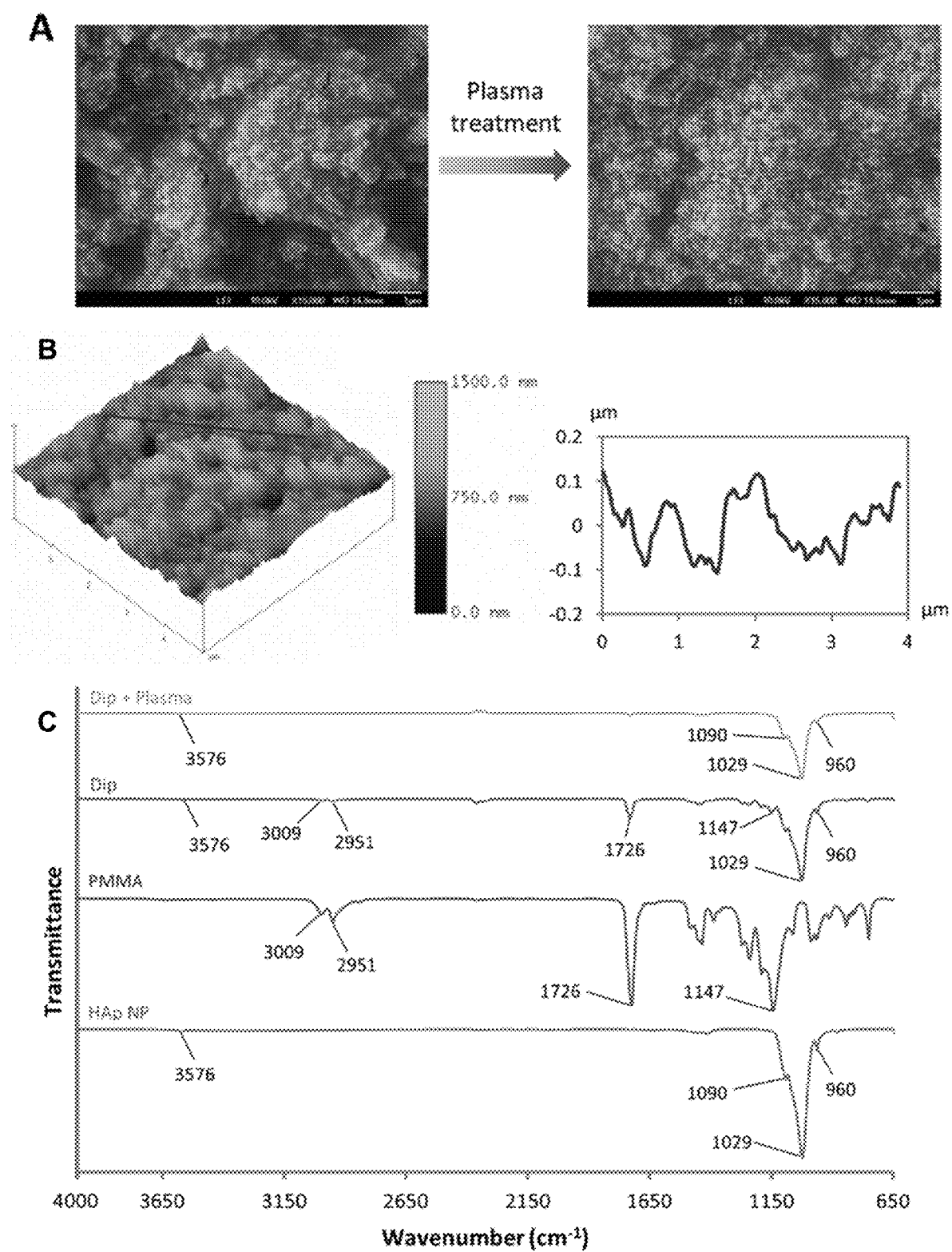
FIG. 5 shows data depicting the surface characterization HAp-immobilized PMMA following plasma treatment.
Figure 5:
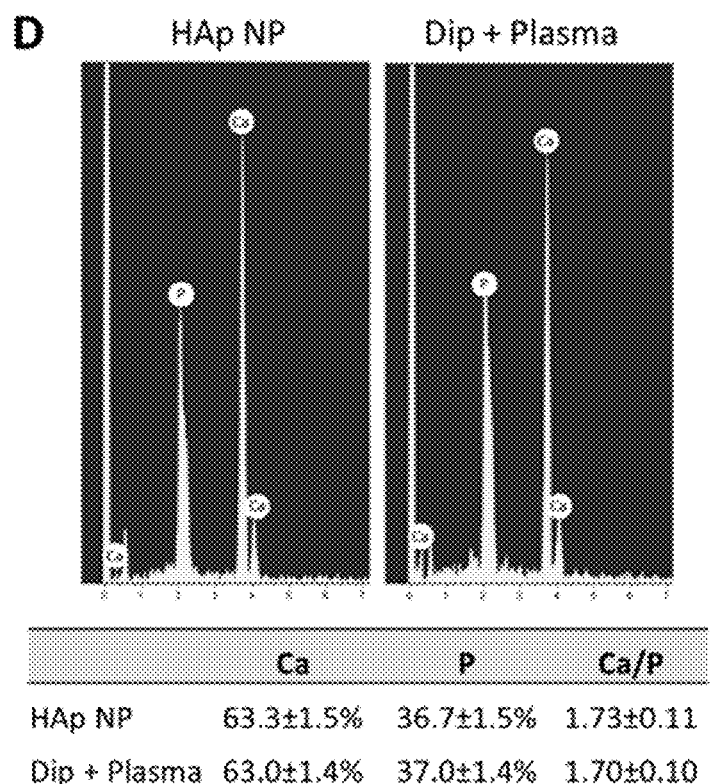
Figure 5:
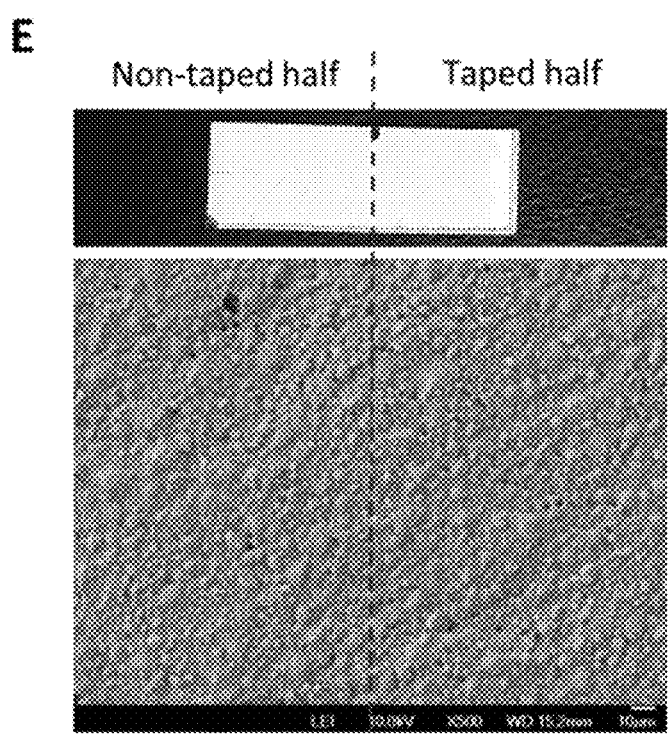

In view of the above, in one example, the nano-powder and the nanoparticle of the present disclosure are not calcium deficient because as exemplified on FIG. 5D, the Ca/P ratio of hydroxyapatite (HAp) nano-powder is 1.73±0.11. Thus, the chemical composition or the Ca/P ration of the layer closely resemble the Ca/P ratio of the nano-powder because in one example, wherein when the bioceramic nanoparticle is hydroxyapatite (HAp) nanoparticle, the Ca/P ratio of the layer is from 1.67 to 1.72. In some examples, wherein when the bioceramic nanoparticle is hydroxyapatite (HAp) nanoparticle, the Ca/P ratio of the layer is about 1.67, or about 1.68, or about 1.69, or about 1.70, or about 1.71, or about 1.72.

In view of all of the foregoing, in one example, the present disclosure provides an optical cylinder of a corneal prosthesis comprising: a) an optical cylinder comprising poly (methyl methacrylate) (PMMA), and b) a plurality of hydroxyapatite (HAp) nanoparticles forming a substantially uniform layer on a circumference of the poly(methyl methacrylate) (PMMA) surface of the optical cylinder.

In one example, the present disclosure provides an optical cylinder of a corneal prosthesis comprising: a) an optical cylinder comprising poly(methyl methacrylate) (PMMA), and b) a plurality of hydroxyapatite (HAp) nanoparticles forming a substantially uniform layer on a circumference of the poly(methyl methacrylate) (PMMA) surface of the optical cylinder, wherein the nanoparticle covers at least 70% of the circumference of the poly(methyl methacrylate) (PMMA) surface of the optical cylinder, wherein the Root Mean Square (RMS) roughness ($R_{RMS}$) value of the layer is from 150 nm to 80 nm, wherein the thickness of the layer is from 30 µm to 100 µm, and wherein the Ca/P ratio of the layer is from 1.67 to 1.72.

In one example, the present disclosure provides an optical cylinder of a corneal prosthesis comprising: a) an optical cylinder comprising poly(methyl methacrylate) (PMMA), and b) a plurality of titanium oxide ($TiO_2$) nanoparticles forming a substantially uniform layer on a circumference of the poly(methyl methacrylate) (PMMA) surface of the optical cylinder In another aspect the present disclosure refers to a corneal prosthesis comprising an optical cylinder as described herein.

The most common technique known in the art for depositing nanoparticles (such as hydroxyapatite (HAp) nanoparticles) on solid polymer is plasma spraying technique. However, plasma spraying technique requires extremely high temperature (>1000° C.) and is not suitable for use in coating solid polymer (such as PMMA), which generally has relatively low melting temperature (for example, the melting temperature of PMMA is 160° C.). As used herein, the term "melting temperature" refers to the temperature at which a solid (such as solid polymer) changes states from solid to liquid at atmospheric temperature. Other nanoparticle coating techniques in the literature, such as the electrophoretic deposition method, and magnetron sputtering, also all require a high temperature that is often higher than the melting temperature of the solid polymer. When nanoparticle coating techniques that are known in the art are used, because the solid polymer is exposed to a temperature that is higher than its melting temperature, the solid polymer may liquefy or melt and thus the characteristic of the solid polymer (such as being optically transparent) may be negatively affected. In view of the above, in order to obtain an alternative optical cylinder of a corneal prosthesis as disclosed herein, there is a need to provide an alternative method for the surface treatment of said optical cylinder.

The inventors of the present disclosure have found an alternative method for the surface treatment of an optical cylinder. Thus, in yet another aspect the present disclosure refers to a method of surface treatment of an optical cylinder of a corneal prosthesis, wherein the method comprises: a) contacting an optical cylinder comprising a solid polymer with a mixture comprising an organic solvent, a dispersant, and a plurality of nanoparticles to form a substantially uniform layer on a circumference of the solid polymer surface of the optical cylinder, and b) removing the organic solvent to immobilize the nanoparticle and the dispersant on the circumference of the solid polymer surface of the optical cylinder, thereby forming the optical cylinder of the corneal prosthesis.

In one example, prior to the contacting in a), the solid polymer may be pretreated by partially or fully submerging the solid polymer into an organic solvent. In one example, the submerging step is followed by removing the solid polymer from the organic solvent. In one example, the contacting in a) may be performed immediately after the pretreatment step. In one example, the contacting in a) may be carried out within a time-frame where the surface of the solid polymer is still liquefied or softened by the organic solvent from the pretreatment step. In one example, the organic solvent in the pretreatment step and in the contacting in a) may be different. In one example, the organic solvent in the pretreatment step and in the contacting in a) may be the same.

In some examples, the contacting in a) may include, but is not limited to, spray coating, dipcoating, and the like. As used herein, the term "coating" refers to the technique of providing nanoparticles on the surface of a polymer or covering the surface of a polymer with nanoparticles. In one example, the contacting in a) is dipcoating. As used herein, the term "dipcoating" refers to a coating process wherein a polymer is partially or fully submerged into a mixture for certain length of time and subsequently removed from the mixture.

The inventors have surprisingly found that dipcoating technique is suitable for treating the surface of an optical cylinder comprising a solid polymer because besides being simple to execute and does not require elaborate and expensive equipment to perform, dipcoating technique is a non-thermal coating technique. Non-thermal coating technique allows for the optical cylinder comprising solid polymer to be contacted with the nanoparticles at a temperature that is lower than the melting temperature of the solid polymer. Thus, the characteristic of the solid polymer (such as being optically transparent) will not be affected because said solid polymer will not be liquefied or will not melt.

Figure 12:
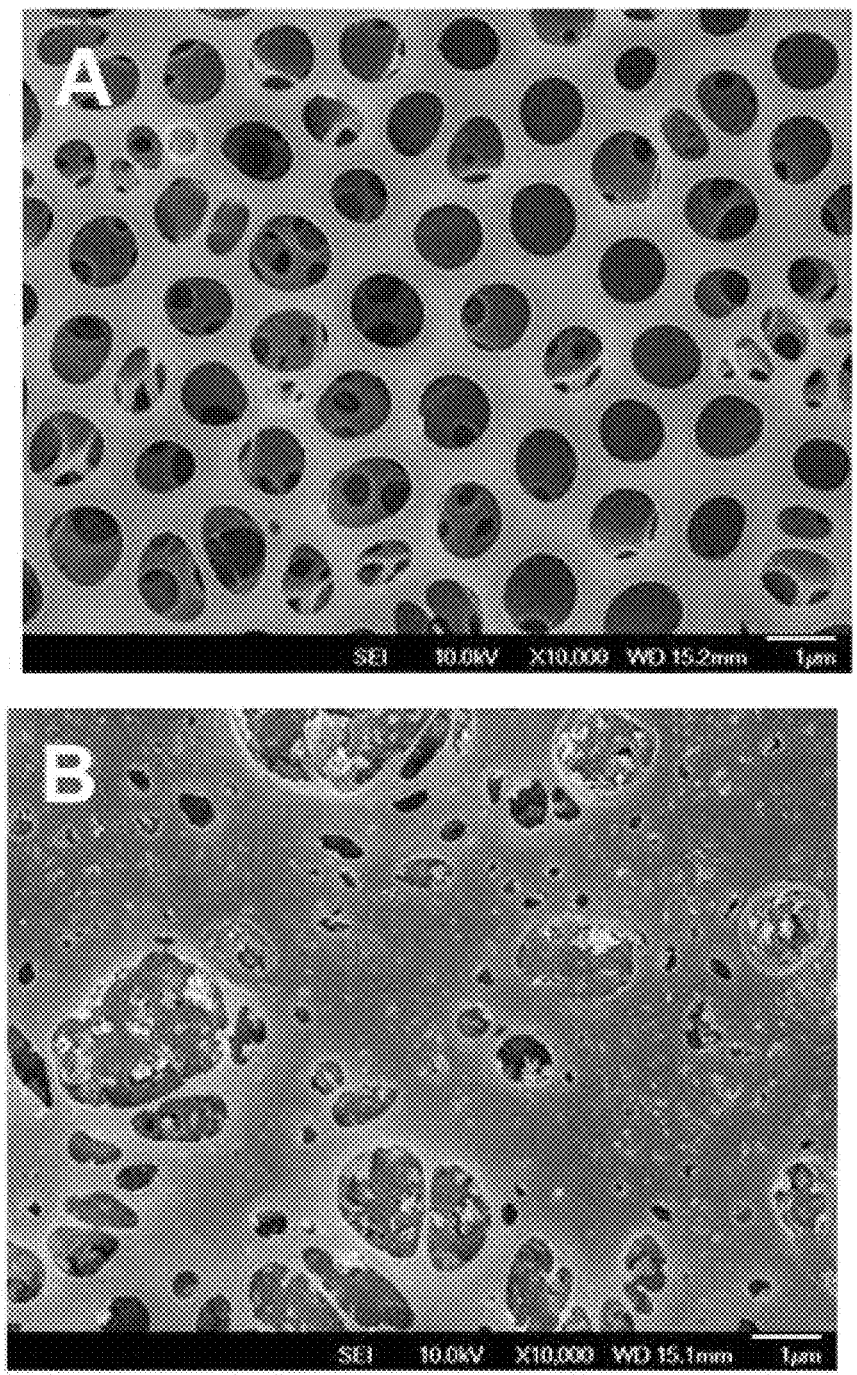
FIG. 12 shows a set of Scanning Electron Microscopy (SEM) results and a photograph depicting the effect of the length of dipcoating time.
Figure 12:
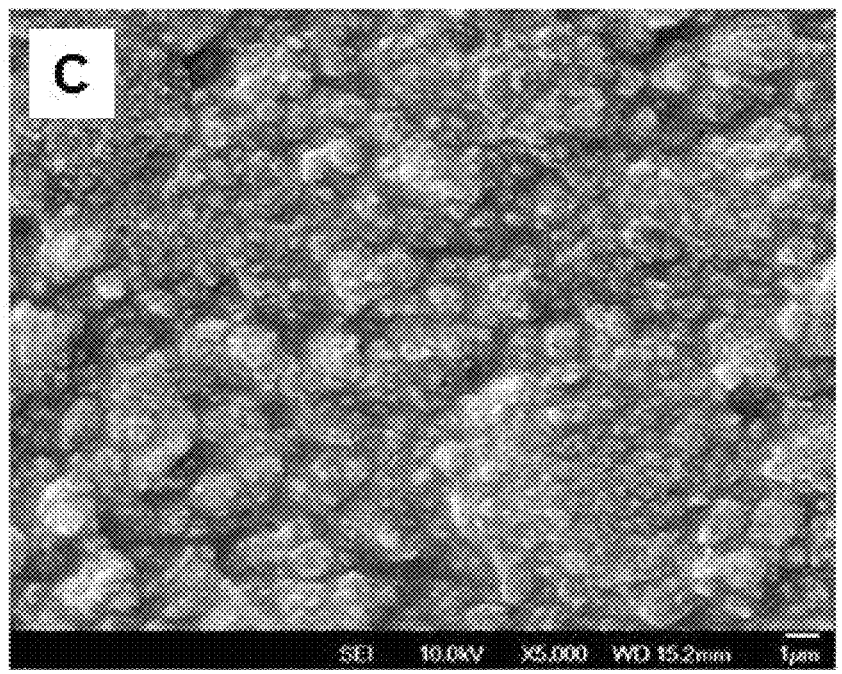
Figure 12:
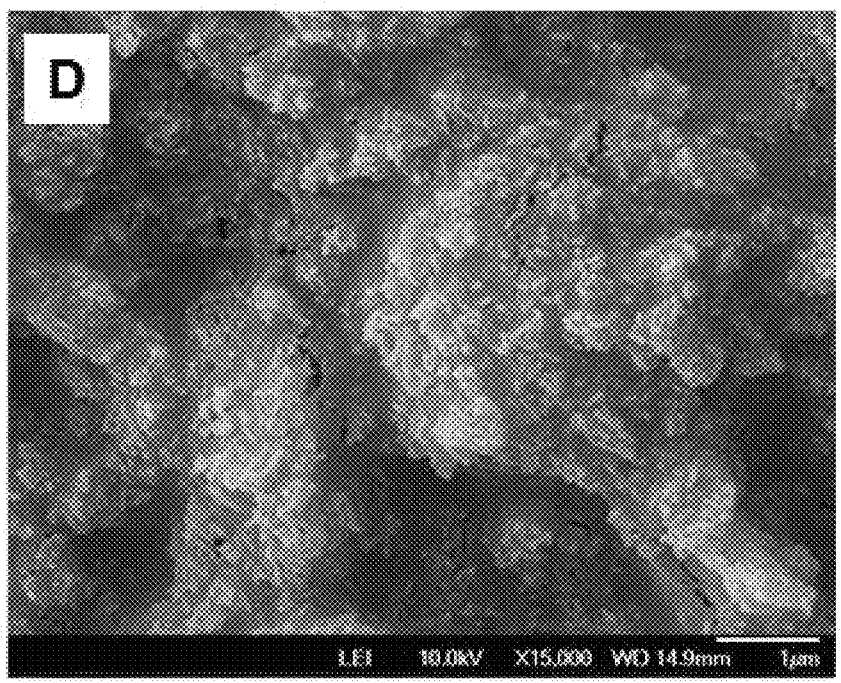
Figure 12:
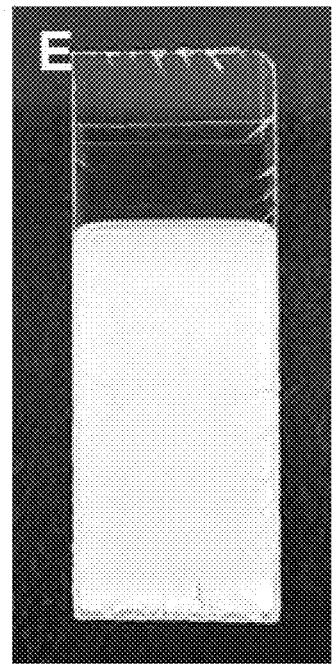
Figure 13:
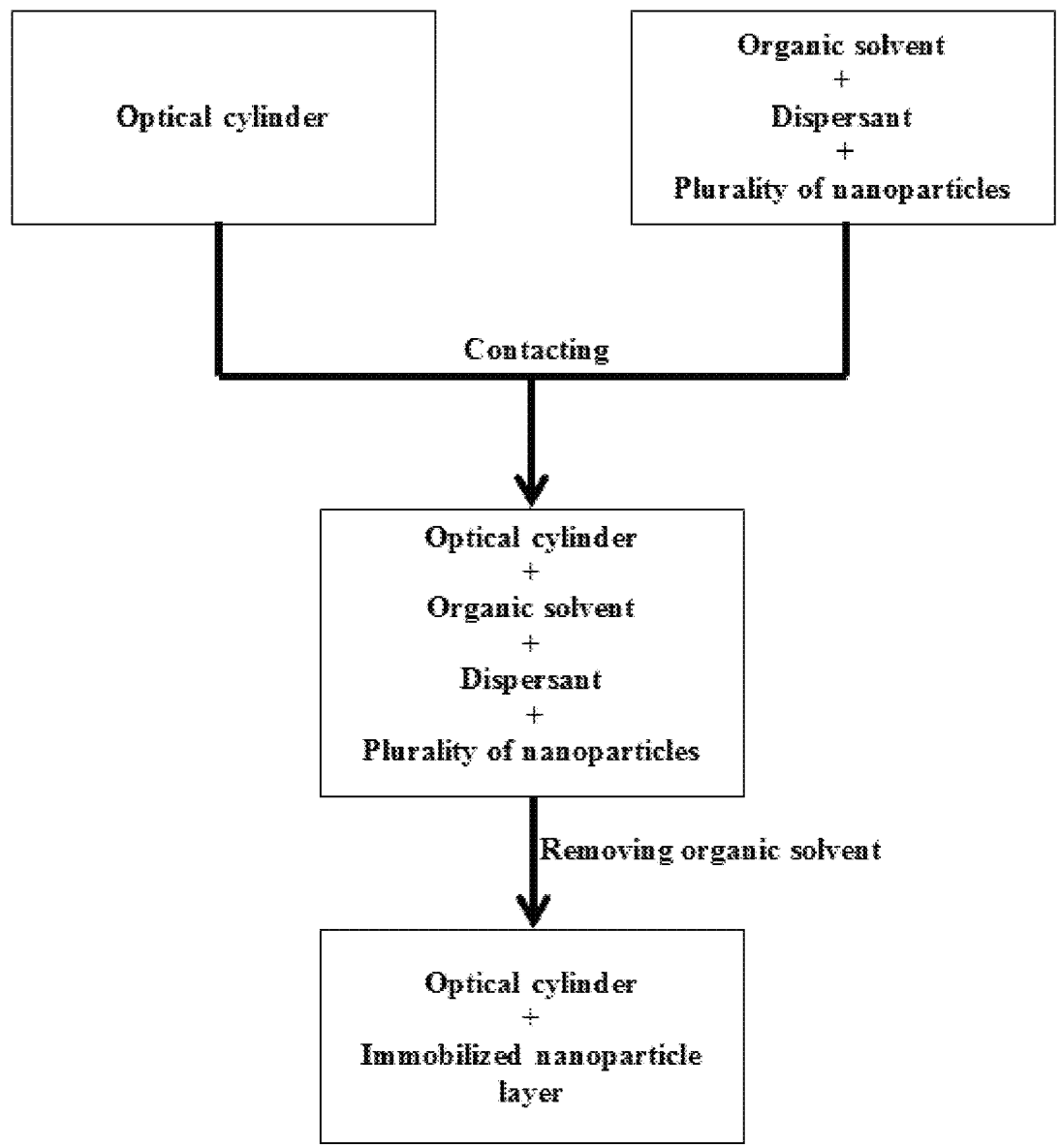
FIG. 13 shows a flowchart depicting an exemplary method for the surface treatment of an optical cylinder of a corneal prosthesis.

Additionally, the inventors have discovered that longer contacting time (such as longer dipcoating time) will allow for the formation of thicker, more compact, and/or more uniform layer because nanoparticles have a tendency to aggregate. For example, FIG. 12C (that corresponds to 1 min (60 seconds) of contacting time) shows a relatively thicker, more compact, and more uniform layer when compared to FIG. 12B (that corresponds to 15 seconds of contacting time). Therefore, in order to be able to form nanoparticles layer having suitable thickness, the inventors have determined that certain lengths of time are needed to contact the optical cylinder with the mixture comprising organic solvent, dispersant, and plurality of nanoparticles. Thus, in some example, the length of time for the contacting the optical cylinder with the mixture (i.e. "the length of time for the contacting in a)") is from 5 seconds to 120 seconds, or from 5 seconds to 115 seconds, or from 15 seconds to 105 seconds, or from 25 seconds to 95 seconds, or from 35 seconds to 85 seconds, or from 45 seconds to 75 seconds, or from 5 seconds to 20 seconds, or from 20 seconds to 40 seconds, or from 40 seconds to 60 seconds, or from 60 seconds to 80 seconds, or from 80 seconds to 100 seconds, or from 100 seconds to 120 seconds, or about 5 seconds, or about 20 seconds, or about 40 seconds, or about 60 seconds, or about 80 seconds, or about 100 seconds, or about 120 seconds. In one example, the length of time for the contacting the optical cylinder with the mixture (i.e. "the length of time for the contacting in a)") is from 45 seconds to 75 seconds. In one example, the length of time for the contacting the optical cylinder with the mixture (i.e. "the length of time for the contacting in a)") is about 60 seconds.

As described herein, in order to form a substantially uniform layer on a circumference of the solid polymer surface of the optical cylinder, the optical cylinder comprising solid polymer is contacted with a mixture comprising an organic solvent, a dispersant, and a plurality of nanoparticles. The organic solvent dissolves the dispersant, the dissolved dispersant disperses the nanoparticles within the organic solvent and prevents the nanoparticles agglomerating and clumping. As exemplified on FIG. 3B, agglomeration and clumping of nanoparticles may cause non-uniform formation of nanoparticle layers.

Having said the above, it is known in the art that organic solvent is generally not biocompatible and thus may damage living cells and living tissue (such as cornea). Therefore, in order to ensure that the optical cylinder is biocompatible, the organic solvent has to be removed. The act of removing or the removal of organic solvent from the optical cylinder that is covered with nanoparticles layer is referred as "the removing in b)" Thus, in some examples, the removing in b) may include, but is not limited to, evaporating, heating, and the like. In one example, the removing in b) is heating. In one example, wherein when the removing in b) is heating, or if the removal of the organic solvent is performed by heating, the heating is performed at a temperature lower than the melting point of the polymer. In one example, the removing in b) is evaporating. The inventors have also found that certain length of time is required to adequately remove the organic solvent from the optical cylinder of the corneal prosthesis. Thus, in some examples, the length of time for the removing in b) is about 10 minutes, or about 20 minutes, or about 30 minutes, or about 40 minutes, or about 50 minutes, or about 1 hour, or about 2 hour, or about 3 hours, or from 10 minutes to 20 minutes, or from 20 minutes to 30 minutes, or from 30 minutes to 40 minutes, or from 40 minutes to 50 minutes, or from 50 minutes to 1 hour, or from 1 hour to 2 hours, or from 2 hours to 3 hours, or from 10 minutes to 3 hours. In one example, when the removing in b) is evaporating, the length of time for the removing in b) is about 30 minutes. In one example, there is no intermediate step(s) between the contacting step (i.e. the step of a) contacting an optical cylinder comprising a solid polymer with a mixture comprising an organic solvent, a dispersant, and a plurality of nanoparticles to form a substantially uniform layer on a circumference of the solid polymer surface of the optical cylinder) and the removal of organic solvent step (i.e. the step of b) removing the organic solvent to immobilize the nanoparticle and the dispersant on the circumference of the solid polymer surface of the optical cylinder).

Additionally, the inventors also surprisingly found that higher concentration of nanoparticles in the mixture creates thicker layer. Thus, in some examples, the concentration of the nanoparticle in the mixture is from 5% (w/v) to 50% (w/v), or from 5% (w/v) to 45% (w/v), or from 5% (w/v) to 35% (w/v), or from 15% (w/v) to 25% (w/v), or from 5% (w/v) to 10% (w/v), or from 10% (w/v) to 15% (w/v), or from 15% (w/v) to 20% (w/v), or from 20% (w/v) to 25% (w/v), or from 25% (w/v) to 30% (w/v), or from 30% (w/v) to 35% (w/v), or from 35% (w/v) to 40% (w/v), or from 40% (w/v) to 45% (w/v), or from 45% (w/v) to 50% (w/v), or about 5% (w/v), or about 10% (w/v), or about 15% (w/v), or about 20% (w/v), or about 25% (w/v), or about 30% (w/v), or about 35% (w/v), or about 40% (w/v), or about 45% (w/v), or about 50% (w/v). In one example, the concentration of the nanoparticle in the mixture is from 15% (w/v) to 25% (w/v). As illustrated for example on Exemplary Method 1, in one example, the concentration of the nanoparticle in the mixture is about 20% (w/v).

Further to the above, the inventor surprisingly found that certain sizes of nanoparticles are suitable for the method of surface treatment disclosed herein. Thus, in some examples, the size of the nanoparticle is from 10 nm to 200 nm, or from 10 nm to 190 nm, or from 10 nm to 180 nm, or from 10 nm to 170 nm, or from 10 nm to 160 nm, or from 20 nm to 150 nm, or from 20 nm to 140 nm, or from 20 nm to 130 nm, or from 20 nm to 120 nm, or from 20 nm to 110 nm, or from 20 nm to 100 nm, or from 10 nm to 20 nm, or from 20 nm to 30 nm, or from 30 nm to 40 nm, or from 40 nm to 50 nm, or from 50 nm to 60 nm, or from 60 nm to 70 nm, or from 70 nm to 80 nm, or from 80 nm to 90 nm, or from 90 nm to 100 nm, or from 100 nm to 110 nm, or from 110 nm to 120 nm, or from 120 nm to 130 nm, or from 130 nm to 140 nm, or from 140 nm to 150 nm, or from 150 nm to 160 nm, or from 160 nm to 170 nm, or from 170 nm to 180 nm, or from 180 nm to 190 nm, or from 190 nm to 200 nm, or about 10 nm, or about 20 nm, or about 30 nm, or about 40 nm, or about 50 nm, or about 60 nm, or about 70 nm, or about 80 nm, or about 90 nm, or about 100 nm, or about 110 nm, or about 120 nm, or about 130 nm, or about 140 nm, or about 150 nm, or about 160 nm, or about 170 nm, or about 180 nm, or about 190 nm, or about 200 nm. In one example, the size of the nanoparticle is from 20 nm to 100 nm. As illustrated in Exemplary Method 1, in one example, wherein when the bioceramic nanoparticle is hydroxyapatite (HAp) nanoparticle, the size of the bioceramic nanoparticle is about 60 nm. As illustrated in Exemplary Method 1, in one example, wherein when the bioceramic nanoparticle is titanium oxide ($TiO_2$), the size of the bioceramic nanoparticle is about 50 nm.

As illustrated in Exemplary Method 2, in one example, the shape of the nanoparticle may include, but is not limited to, needle (rod) shape, spherical shape, and the like. As illustrated in Exemplary Method 2, in one example, wherein when the bioceramic nanoparticle is hydroxyapatite (HAp) nanoparticle, the shape of the nanoparticles is needle (rod) shape. As illustrated in Exemplary Method 2, in one example, wherein when the bioceramic nanoparticle is titanium oxide ($TiO_2$), the shape of the nanoparticle is spherical shape.

As described herein, the mixture that is contacted with the optical cylinder comprising solid polymer comprises an organic solvent, a dispersant, and a plurality of nanoparticles. As used herein, the term "dispersant" refers to a substance added to a suspension or a mixture to improve the separation of particles and to prevent settling or clumping. The inventors have surprisingly found that the dispersant should be made of the same material as the solid polymer because besides dispersing the nanoparticles in the organic solvent, the dispersant also acts as a glue to adhere the nanoparticle layer on the polymer. Without wishing to be bound by theory, it is believed that using dispersant from another material may cause incompatibility and increase the risk of delamination of the nanoparticle layer. Thus, in some examples, the solid polymer and the dispersant may include, but is not limited to, poly(methyl methacrylate) (PMMA), polystyrene, polycarbonate, polythiourethane, polyethylene terephthalate, polypropylene, and the like. As exemplified on Exemplary Method 1 and Exemplary Method 2, in one example, the solid polymer and the dispersant is poly (methyl methacrylate) (PMMA).

Further to the above, the inventor surprisingly found that certain concentrations of dispersant in the mixture are suitable for the method of surface treatment disclosed herein. Thus, in some examples, the concentration of the dispersant in the mixture is from 2% (w/v) to 10% (w/v), or from 2% (w/v) to 9% (w/v), or from 2% (w/v) to 8% (w/v), or from 3% (w/v) to 7% (w/v), or from 4% (w/v) to 6% (w/v), or from 2% (w/v) to 4% (w/v), or from 4% (w/v) to 7% (w/v), or from 7% (w/v) to 10% (w/v), or about 1% (w/v), or about 2% (w/v), or about 3% (w/v), or about 4% (w/v), or about 5% (w/v), or about 6% (w/v), or about 7% (w/v), or about 8% (w/v), or about 9% (w/v), or about 10% (w/v). In one example, the concentration of the dispersant in the mixture is from 4% (w/v) to 6% (w/v). As illustrated for example on Exemplary Method 1 and Exemplary Method 2, in one example, the concentration of the dispersant in the mixture is about 5% (w/v).

In some examples, wherein when the dispersant is poly (methyl methacrylate) (PMMA), the molecular weight (MW) of the dispersant is from 100,000 Dalton (Da) to 140,000 Da, or from 110,000 Da to 130,000 Da, or from 115,000 Da to 125,000 Da, or from 100,000 Da to 110,000 Da, or from 110,000 Da to 120,000 Da, or from 120,000 Da to 130,000 Da, or from 130,000 Da to 140,000 Da, or about 100,000 Da, or about 110,000 Da, or about 120,000 Da, or about 130,000 Da, or about 140,000 Da. In one example, wherein when the dispersant is poly(methyl methacrylate) (PMMA), the molecular weight (MW) of the dispersant is about 120,000 Da.

Without wishing to be bound by theory, it is believed that the organic solvent used in the mixture comprising an organic solvent, a dispersant, and a plurality of nanoparticles acts to liquefy or soften the surface of the solid polymer thereby creating craters that trap and immobilize the nanoparticles. The inventors surprisingly found that certain organic solvents are capable to liquefy or soften the surface of the solid polymer. Thus, in some example, the organic solvent may include, but is not limited to chloroform ($CHCl_3$), dichloromethane ($CH_2Cl_2$), acetone, toluene, and tetrahydrofuran (THF), dimethylformamide (DMF), tetrachloromethane (carbon tetrachloride), 1,4-dioxane, xylene, cyclohexanone, ethyl acetate, diethyl carbonate, and the like. As illustrated on Exemplary Method 1 and Exemplary Method 2, in one example, the organic solvent is chloroform ($CHCl_3$).

As used herein, the term "organic solvent" refers to carbon-based solvents that are capable of dissolving or dispersing one or more other substances. In one example, the organic solvent dissolves or is capable of dissolving solid polymer such as poly(methyl methacrylate) (PMMA). The organic solvent that dissolves solid polymer such as poly (methyl methacrylate) (PMMA) generally comprises of organic compounds having halogen such as Chlorine (Cl), organic compounds having benzene ring, or cyclic compounds.

Further to the above, the inventors have surprisingly found that unmasking of nanoparticles that may have been masked by the dispersant and creating a smoother and more even surface on the nanoparticle layer are beneficial in forming a substantially uniform layer on a circumference of the solid polymer surface of the optical cylinder. The unmasking and the creation of a smoother and more even surface may be performed using any methods known in the art. Thus, in one example, the method further comprises exposing the layer to a plasma treatment. As illustrated in Exemplary Method 2, in some example, the plasma may include, but is not limited to, argon plasma, oxygen plasma, and the like. As illustrated in Exemplary Method 1, in one example, the plasma may be oxygen plasma.

Further to the above, the inventors have found that the length of time for the plasma treatment has to be conducted at certain length of time. Thus, in some example, the length of time for exposing is from 30 seconds to 300 seconds, or from 30 seconds to 60 seconds, or from 60 seconds to 90 seconds, or from 90 seconds to 120 seconds, or from 120 seconds to 150 seconds, or from 150 seconds to 180 seconds, or from 180 seconds to 210 seconds, or from 210 seconds to 240 seconds, or from 240 seconds to 270 seconds, or from 270 seconds to 300 seconds, or about 30 seconds, or about 60 seconds, or about 90 seconds, or about 120 seconds, or about 150 seconds, or about 180 seconds, or about 210 seconds, or about 240 seconds, or about 270 seconds, or about 300 seconds. In one example, the length of time for exposing is from 30 seconds to 300 seconds. As illustrated in Exemplary Method 1, in one example, the length of time for exposing is about 30 seconds. As illustrated in Exemplary Method 2, in one example, the length of time for exposing is about 120 seconds.

In view of all of the foregoing, in one example, the present disclosure refers to a method of surface treatment of an optical cylinder of a corneal prosthesis, wherein the method comprises: a) dipcoating an optical cylinder comprising poly(methyl methacrylate) (PMMA) with a mixture comprising chloroform ($CHCl_3$), a dispersant comprising poly (methyl methacrylate) (PMMA), and a plurality of hydroxyapatite (HAp) nanoparticles or titanium oxide ($TiO_2$) nanoparticles to form a substantially uniform layer on a circumference of the poly(methyl methacrylate) (PMMA) surface of the optical cylinder, and b) evaporating the chloroform ($CHCl_3$) to immobilize the hydroxyapatite (HAp) nanoparticle or the titanium oxide ($TiO_2$) nanoparticle and the dispersant on the circumference of the poly (methyl methacrylate) (PMMA) surface of the optical cylinder, thereby forming the optical cylinder of the corneal prosthesis.

In one example, the present disclosure refers to a method of surface treatment of an optical cylinder of a corneal prosthesis, wherein the method comprises: a) dipcoating an optical cylinder comprising poly(methyl methacrylate) (PMMA) with a mixture comprising chloroform ($CHCl_3$), a dispersant comprising poly(methyl methacrylate) (PMMA), and a plurality of hydroxyapatite (HAp) nanoparticles or titanium oxide ($TiO_2$) nanoparticles to form a substantially uniform layer on a circumference of the poly(methyl methacrylate) (PMMA) surface of the optical cylinder, and b) evaporating the chloroform ($CHCl_3$) to immobilize the hydroxyapatite (HAp) nanoparticle or the titanium oxide ($TiO_2$) nanoparticle and the dispersant on the circumference of the poly(methyl methacrylate) (PMMA) surface of the optical cylinder, wherein the method further comprises exposing the layer to an oxygen plasma treatment, thereby forming the optical cylinder of the corneal prosthesis.

In one example, the present disclosure refers to a method of surface treatment of an optical cylinder of a corneal prosthesis, wherein the method comprises: a) dipcoating an optical cylinder comprising poly(methyl methacrylate) (PMMA) with a mixture comprising chloroform ($CHCl_3$), a dispersant comprising poly(methyl methacrylate) (PMMA), and a plurality of hydroxyapatite (HAp) nanoparticles or titanium oxide ($TiO_2$) nanoparticles to form a substantially uniform layer on a circumference of the poly(methyl methacrylate) (PMMA) surface of the optical cylinder, and b) evaporating the chloroform ($CHCl_3$) to immobilize the hydroxyapatite (HAp) nanoparticle or the titanium oxide ($TiO_2$) nanoparticle and the dispersant on the circumference of the poly(methyl methacrylate) (PMMA) surface of the optical cylinder, thereby forming the optical cylinder of the corneal prosthesis. In one example, the length of time for the dipcoating is about 60 seconds or is 60 seconds. In one example, the length of time for the evaporating is about 30 minutes or is 30 minutes. In one example, the method further comprises exposing the layer to an oxygen plasma treatment, wherein the length of time for is about 30 seconds or is 30 seconds. In one example, the method further comprises exposing the layer to an oxygen plasma treatment, wherein the length of time for is about 120 seconds or is 120 seconds.

In yet another aspect, the present disclosure refers to an optical cylinder of a corneal prosthesis obtainable by the method disclosed herein.

As used herein, the term "about" in the context of concentration of a substance, size of a substance, length of time, or other stated values means +/−5% of the stated value, or +/−4% of the stated value, or +/−3% of the stated value, or +/−2% of the stated value, or +/−1% of the stated value, or +/−0.5% of the stated value.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Material and Methods
Immobilization of Nanoparticles on the PMMA Surface.

PMMA sheets with 0.5 mm thickness were purchased from Goodfellow (Huntingdon, England). The sheet was cut into 0.5×2 cm pieces, washed in 70% ethanol for 15 min, and rinsed extensively with distilled water before being dried in a 37° C. vacuum incubator for 24 h. Several concentrations of needle-shaped, 60 nm HAp nanoparticles (MKnano, Missisauga, Canada), 0%, 10%, and 20% (w/v), were mixed into chloroform without PMMA or with 5% (w/v) PMMA (MW 120 000; Sigma-Aldrich, St. Louis, Mo.). The mixture was then probe sonicated for 5 min at 50% amplification level with a 5 s pause every 30 s to allow for gentle shaking. Immobilization of the HAp nanoparticles on the PMMA sheet was performed by dip coating technique using a KSV NIMA dip coater (Biolin Scientific, Stockholm, Sweden). The PMMA sheet was secured with a custom-made clamp and dipped for 5, 15, 30, or 60 s. The PMMA sheet was both lowered and withdrew with a speed of 240 mm/min. Following this, the coated PMMA sheet was left on the dip coater for 30 min to allow for evaporation of the chloroform and nanoparticle settlement at the surface. The substrate was then washed with 70% ethanol, rinsed with copious amounts of distilled water, and dried in a 37° C. vacuum incubator overnight.

The following day, the surface of the substrates was subjected to oxygen plasma treatment to remove contaminants that had masked the HAp surface during the dip coating process. Oxygen plasma treatment was performed in a Covance multipurpose plasma system (Femto Science, South Korea). The samples were treated with radio frequency oxygen plasma with 200 W power for 30 s. The PMMA sheets were placed between two parallel plate electrodes enclosed in the plasma reactor chamber. Air was removed with vacuum application for at least 30 min before the power was turned on. The pressure at the moment of plasma discharge was 0.2 Torr. The flow rate of oxygen was set at 20 $cm^3$/min. After the discharge stopped, the plasma-treated PMMA sheets were removed from the plasma chamber, washed with 70% ethanol and copious amounts of distilled water, and dried in a 37° C. vacuum incubator overnight before being used for further experiments.
Analysis of Surface Morphology and Elemental Composition.

Surface morphology and roughness of functionalized PMMA sheets were observed with a Nanoscope IIIa AFM (Digital Instruments, Santa Barbara, Calif.). Topographic images were captured in tapping mode employing a monolithic silicon NCH-50 Point Probe (NanoWorld AG, Neuchatel, Switzerland). The surface lateral roughness profile was generated from the AFM height images by using Gwyddion software version 2.45 (Czech Metrology Institute, Brno, Czech Republic). In addition to AFM, the surface morphology of HAp nanoparticle-immobilized PMMA sheets was also analyzed by SEM. In brief, the PMMA sheets were mounted on a stub secured by carbon adhesive tape. The sheets were sputter-coated with a 10 nm thick layer of gold and examined with a JSM-7600F microscope (JEOL, Tokyo, Japan). Cross-sectioned samples were prepared by cryo-fracturing in liquid nitrogen to analyze the depth of penetration of the nanoparticles into the bulk of the PMMA. Surface elemental composition was assessed by EDX attached to the microscope.
Analysis of Surface Functional Groups by ATR-FTIR.

Infrared (IR) spectra of the modified PMMA surfaces were collected using a Perkin Elmer Frontier FTIR spectrometer (Waltham, Mass.). The spectrometer was equipped with an ATR sampling universal accessory supplied with a top plate for ZnSe crystal. The PMMA sheet was placed on the plate and tightened down to the 40% gauge mark shown on the software for the instrument. Spectra were obtained with 16 scans and 4 $cm^{-1}$ resolution.
Casting of Collagen Hydrogel on PMMA.

Casting of collagen hydrogel on the modified PMMA surfaces was performed after the substrates had been dried for 24 h in a 37° C. vacuum incubator. The collagen hydrogel was constructed as described previously. Bovine atelocollagen type I was purchased from Koken (Tokyo, Japan). Briefly, a 0.5 mL aliquot of 10% (w/v) atelocollagen in acidic solution (pH 3.0) was loaded into a syringe mixing system. The collagen solution was adjusted to pH 5.0 with 1 N NaOH, followed by thorough mixing by pumping the syringes. Calculated amounts of 10% (w/v) 1-ethyl-3-(3-(dimethylamino)propyl)carbodiimide (EDC; Sigma-Aldrich) and 10% (w/v) N-hydroxysuccinimide (NHS; Sigma-Aldrich) were added to produce a 2:1 molar ratio of EDC to NHS and mixed with the collagen solution. The mixed solution was dispensed into a 5 mm diameter silicone mold on the center of the PMMA sheet. The hydrogel was cured in a humidified chamber at room temperature for 24 h before further experiments.

Shear Adhesion Strength Test.

Samples (n=6 of each group) were secured at the base of a Chatillon tensile tester (Largo, Fla.). The position of the sample was adjusted until the chisel-shaped fixture (attached to 10 N load cell) aligned at the center of the hydrogel at the bonding interface. The crosshead speed was set at 5 mm/min. The test was stopped, and maximum force was recorded when the hydrogel was completely detached from the surface of PMMA sheets. To study the stability of the bonding in a longer term, the hydrogel-PMMA constructs were incubated in pH 7.4 artificial tear fluid (ATF) at 37° C. for 14 and 28 days, with the ATF refreshed daily. ATF was prepared as previously described by mixing 68 g of NaCl, 22 g of $NaHCO_3$, 0.08 g of $CaCl_2.2H_2O$, and 14 g of KCl in 1000 mL of distilled water.

Thermogravimetric Analysis to Detect the Presence of Chloroform.

Thermogravimetric analysis (TGA) using TGA Q500 (TA Instruments, New Castle, Del.) was performed to detect the presence of residual chloroform. TGA was carried out for pristine PMMA and HAp nanoparticle-immobilized PMMA sheets with 10° C./min temperature increment from 25 to 800° C. in nitrogen atmosphere.

Statistical Analysis.

Data were expressed as mean±standard deviation (SD). Statistical significance between groups was calculated by one-way ANOVA and post hoc Tukey comparison test. A value of p<0.05 was considered to be statistically significant. All statistical analysis was performed using SPSS software (version 17.0, SPSS Inc., Chicago, Ill.).

Experimental Result

To demonstrate the poor coating retention of the coating layer as known in the art, a delamination test by applying Scotch filament tape 892 (with 65.4N/100 mm adhesion strength rating) on d-CaP surface followed by removal of the tape the following day showed complete delamination of the coating (FIG. 2A). Poor coating retention was probably due to the underlying dopamine and 11-MUA (laid before CaP deposition) did not form a homogeneous coating layer. Aggregates of the coating could be seen interspersed on the PMMA surface (FIG. 2B). This led to weak anchorage of the CaP layers on some regions of the PMMA not coated by the dopamine. In addition, the crystallinity and purity of the SBF-assembled CaP were poor, where the calcium deficient bone-like apatite exhibited a lower Ca/P ratio than HAp (FIG. 2C). Poor CaP crystallinity and purity are associated with increased resorption rate of the apatite, reducing the longevity of the SBF-mediated CaP coating in biological microenvironment.[13,14] Illustrations in FIG. 2D summarized the combination of non-homogenous poly-dopamine layer and desorption of the CaP layers led to reduced adhesion of collagen on d-CaP surface.

Figure 3:
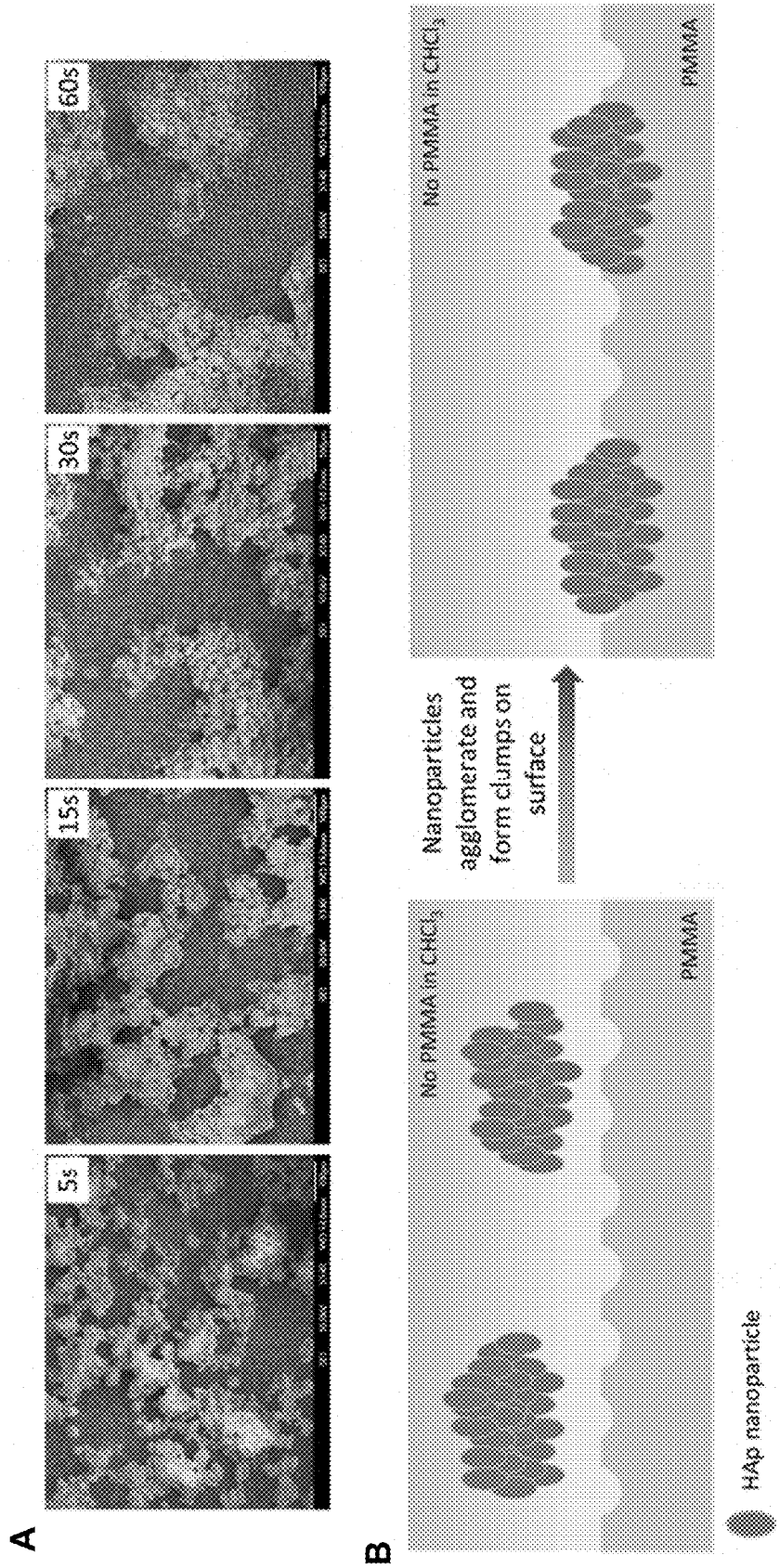
FIG. 3 shows data depicting the effect of the use of dispersant such as 5% (w/v) PMMA in the dipcoating mixture.
Figure 3:
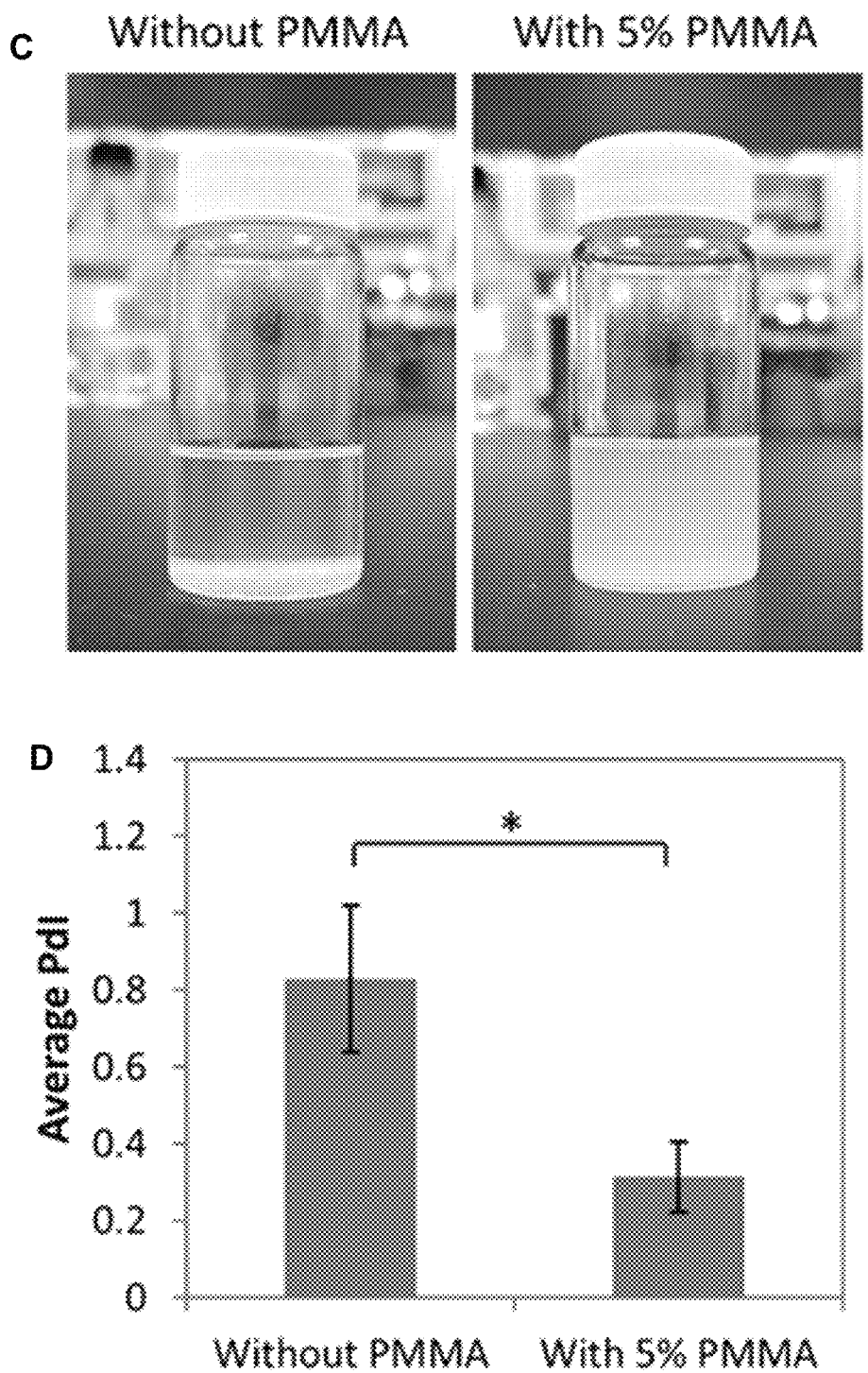

Unlike the disclosure in the prior art, the dipcoating technique disclosed herein utilized a dispersant (such as 5% (w/v) PMMA) in any organic solvent (e.g. chloroform or dichloromethane) as dispersant for the nanoparticles (such as HAp nanoparticles). The addition of PMMA in the solvent reduces the agglomeration propensity of the nanoparticles in the dipcoating solution, providing ample time for the dispersed HAp to be laid on the surface in a more uniform and homogenous fashion. Without PMMA, it resulted in clumps of HAp nanoparticles on the PMMA surface. Prolonging the dipcoating process to 60 s also did not improve the homogeneity of the coating (FIGS. 3A and 3B). Craters could be seen on areas that were not covered by the HAp (FIG. 3A). FIG. 3C (left panel) clearly showed that most nanoparticles that were added in the chloroform solution had already settled at the bottom of the glass container after 30 minutes. In contrast, the nanoparticles were still relatively dispersed in the chloroform that had been added with 5% (w/v) PMMA after 30 minutes (FIG. 3C, right panel). Nanozetasizer revealed a polydispersity index (PdI) of 0.828±0.191 when PMMA was not added into the solvent, which was significantly higher than the PdI of the mixture when 5% PMMA was added (0.313±0.090; p=0.002) (FIG. 3D).

Figure 4:
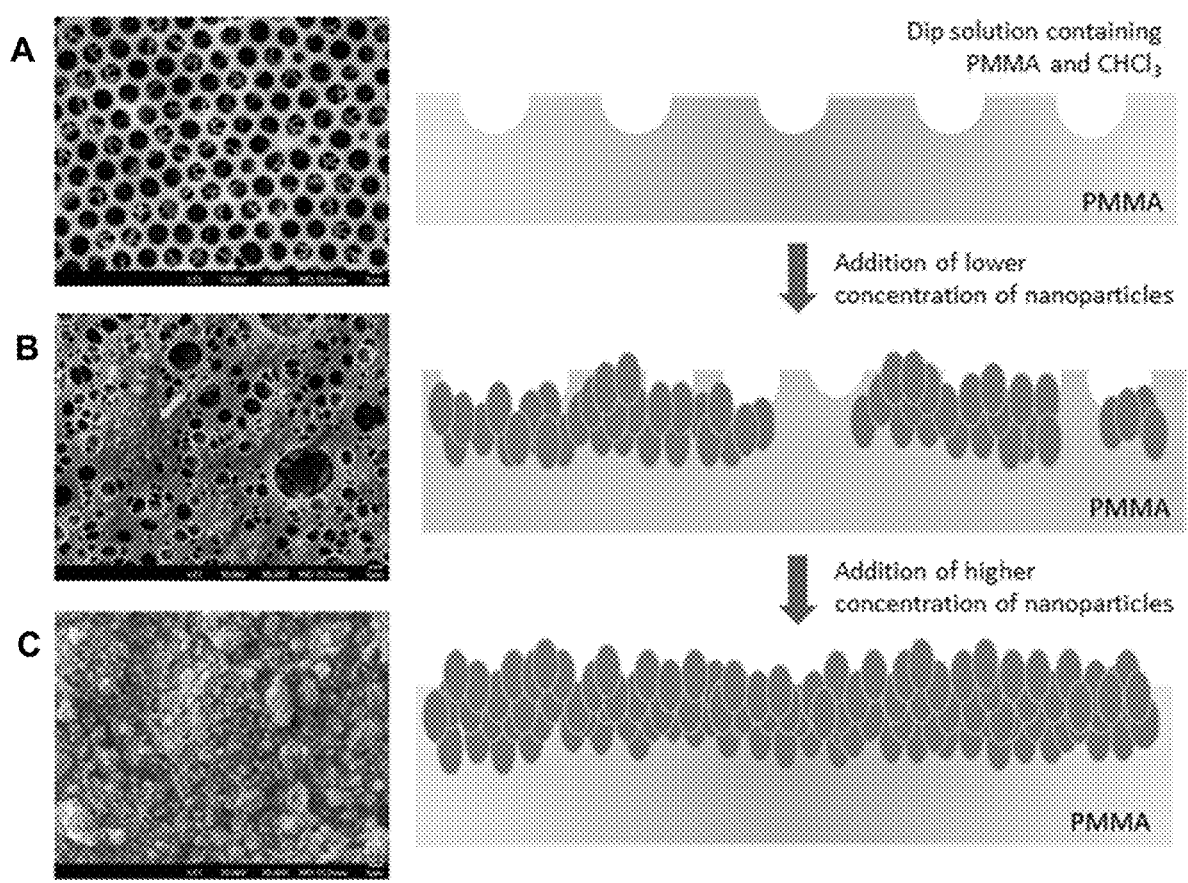
FIG. 4 shows a set of Scanning Electron Microscopy (SEM) results and graphical illustrations depicting the dip-coating technique mechanism in immobilizing HAp nanoparticles.
Figure 6:
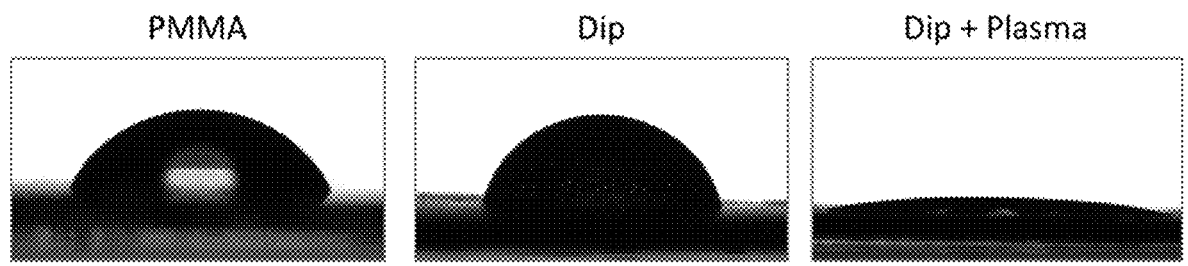
FIG. 6 shows a set of photographs depicting comparison of surface hydrophilicity of untreated PMMA, HAp-coated PMMA, and post-plasma treated HAp-coated PMMA. Thus.

The use of organic solvent, in addition for dissolving the PMMA as described in the preceding paragraph, acts to liquify or "soften" the surface of PMMA substrate (PMMA sheet), creating craters (FIG. 4A), that trap and immobilize the nanoparticles (FIG. 4B). The longer the dipcoating time, the higher the concentration of the nanoparticles added in the dipcoating solution, the thicker and more compact the HAp layer becomes due to the tendency of the HAp nanoparticles to aggregate (FIG. 4C). At the completion of dipcoating (after being lifted up from the coating solution), the chloroform evaporates and PMMA re-solidifies, immobilizing the HAp nanoparticles that were trapped in the craters earlier. Following the dipcoating process, plasma treatment was performed on the HAp-immobilized PMMA surface to remove contaminants and PMMA that might have masked the nanoparticles and also to even the surface out (FIGS. 5A and 5B). The plasma treated surface was relatively smoother than pre-treated substrate (Table 1). Prominent IR spectra of PMMA, i.e. peaks near 1100-1300 $cm^{-1}$ and 1726 $cm^{-1}$, which were due to the presence of C—O and C=O stretching modes of the ester group, respectively, as well as spectral peaks at 2951 and 3009 $cm^{-1}$ which indicated the $CH_2$ group of PMMA were present in much weaker intensity after plasma treatment (FIG. 5C). The HAp nanoparticles-immobilized PMMA surface featured spectral peaks that resembled more closely to HAp, i.e. peaks at 960, 1029 and 1090 $cm^{-1}$ which were attributed to the phosphate groups and a peak at 3576 $cm^{-1}$ which was indicative of the hydroxyl group of HAp (FIG. 5C). To simplify the term for plasma irradiated HAp-immobilized substrate, this study group is henceforth referred to as HAp-coated PMMA. In addition to changes in surface roughness and chemistry, surface hydrophilicity was also altered from 79.2±5.6° before plasma treatment to 14.3±3.4° after treatment (p<0.001) (FIG. 6). The HAp-coated PMMA surface was also significantly more hydrophilic than untreated PMMA (66.1±0.5°; p=0.006) (FIG. 6). The dip coating process and subsequent plasma treatment did not significantly alter the Ca/P ratio of the HAp (p=0.688) (FIG. 5D). Furthermore, the HAp nanoparticles immobilized on the PMMA appeared to be anchored strongly to the surface. Tape adhesion test, similar to that carried out by earlier on CaP-coated PMMA, shown in FIG. 2 above, did not delaminate the HAp-coated PMMA surface (FIG. 5E). Using image processing and mean gray values calculation tools in the ImageJ software, it was demonstrated that 77±5% of the surface was populated by the HAp nanoparticles (FIG. 7). By processing high magnification SEM images with ImageJ, areas which were not covered by the nanoparticles could be differentiated (black background) (FIG. 7). By processing high magnification SEM images with ImageJ, areas which were not covered by the nanoparticles could be differentiated (black background).

TABLE 1

Surface roughness of pristine PMMA, dipcoated PMMA and plasma treated dipcoated PMMA.

| Treatment | RMS (nm) | p value* | $R_{max}$ (nm) | p value* |
|---|---|---|---|---|
| Pristine PMMA | 1.5 ± 0.3 | <0.001 | 38.1 ± 4.8 | <0.001 |
| Dip | 102.2 ± 14.4 | | 797.3 ± 164.8 | |
| Dip + Plasma | 92.5 ± 10.5 | 0.213 | 787.5 ± 87.9 | 0.900 |

Figure 8:
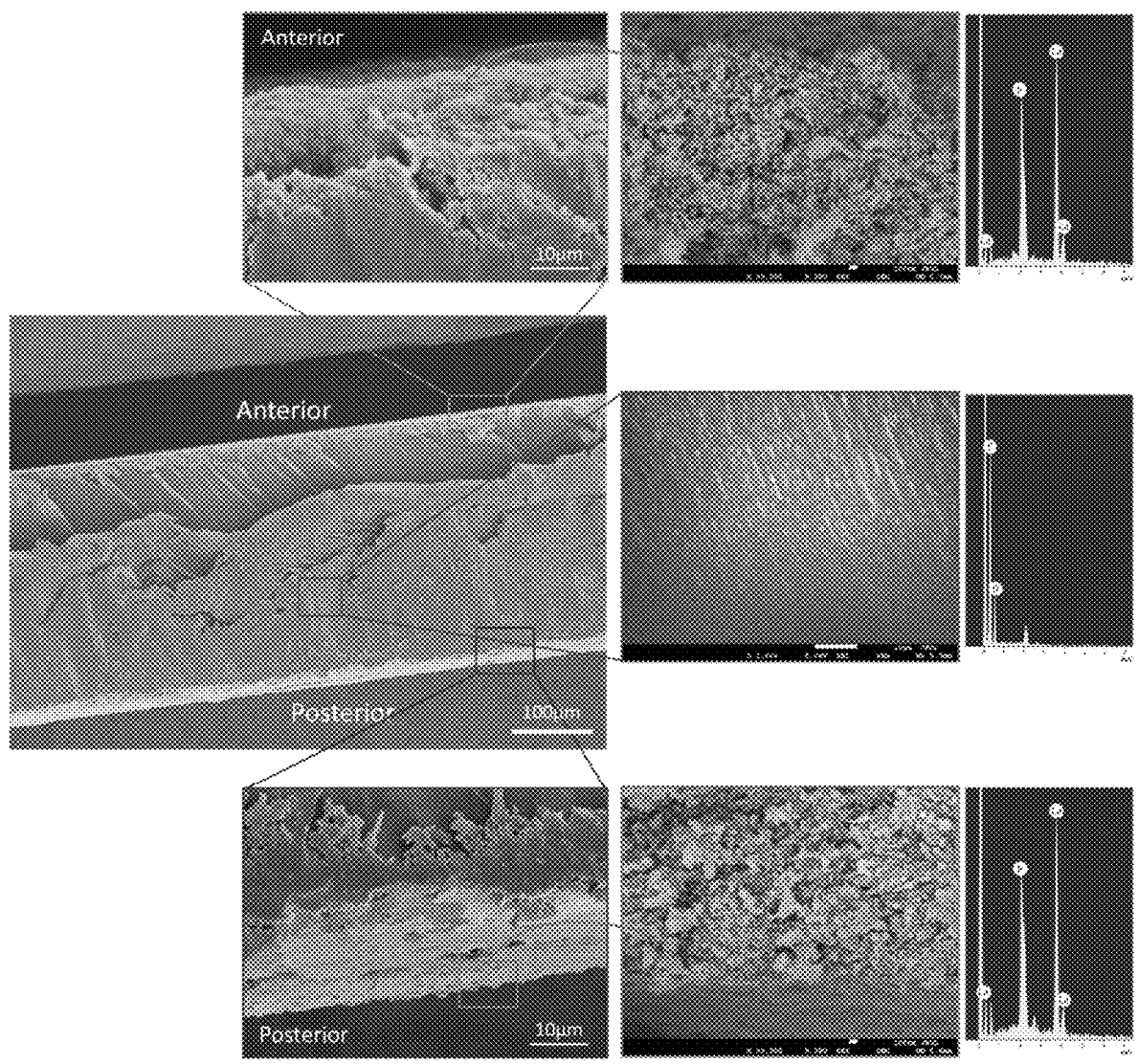
FIG. 8 shows a set of Scanning Electron Microscopy (SEM) results and Energy-dispersive X-ray spectroscopy (EDX) results depicting cross-section of plasma treated HAp-coated PMMA. Electron-intense layers, suggesting the presence of HAp, along the anterior and posterior surfaces of the PMMA. Individual rod shaped nanoparticles could easily be seen in high magnification (30,000×) images. SEM on the bulk of the PMMA did not reveal the presence of HAp nanoparticles. EDX analysis further confirmed that HAp (Ca and P elements) could only be detected at the surfaces of the PMMA, but not in the bulk of the PMMA. Thus.
Figure 9:
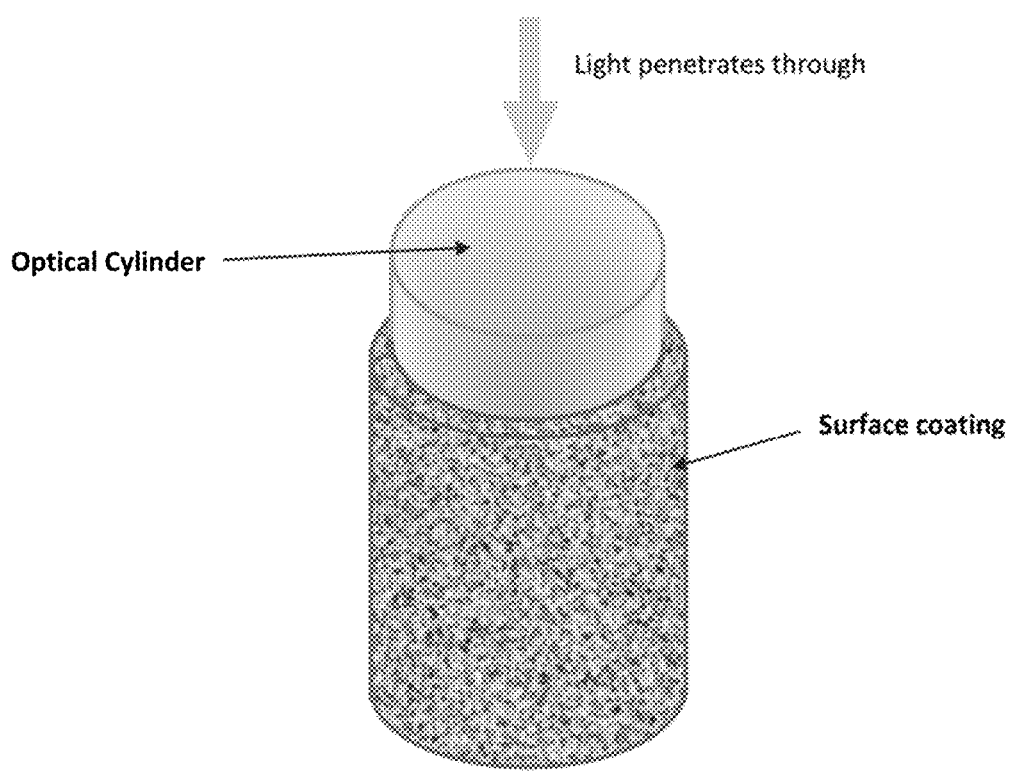
FIG. 9 shows a graphical illustration depicting schematic of the surface coating outcome for a KPro optical cylinder. The coating process results in thin coating that wraps around the circumference of the solid polymer surface of the optical cylinder. The surface coating or nanoparticles do not penetrate deep into the solid polymer and do not interefere with the visual axis of the patient. The bulk of the optical cylinder is unaffected by the surface treatment (such as dipcoating) process and remains clear, allowing light to penetrate through the center of the optic to allow for vision.

*Significant difference relative to 60 s treatment time in respective formulation The low magnification cross-sectional SEM image showed that the HAp did not penetrate deep into the PMMA (FIG. 8). HAp, which appeared as electron-intense layers both anteriorly and posteriorly, was only observed at 30-50 μm depth from the surface. In contrast, the center of the PMMA appeared relatively smooth and no presence of HAp nanoparticles. EDX further confirmed that Ca and P elements were only detectable at the surfaces of the PMMA, whereas only C and O elements were found in the center of the PMMA (FIG. 8). High magnification images of both anterior and posterior surfaces of the HAp-coated PMMA revealed presence of rod shaped nanoparticles, consistent with the shape of the nanoparticles used in this study (FIG. 8). This suggests that the dipcoating process results in thin coating that wraps around the PMMA substrate, therefore permitting light to penetrate through the center of the optic to allow for vision (FIG. 9).

Figure 10:
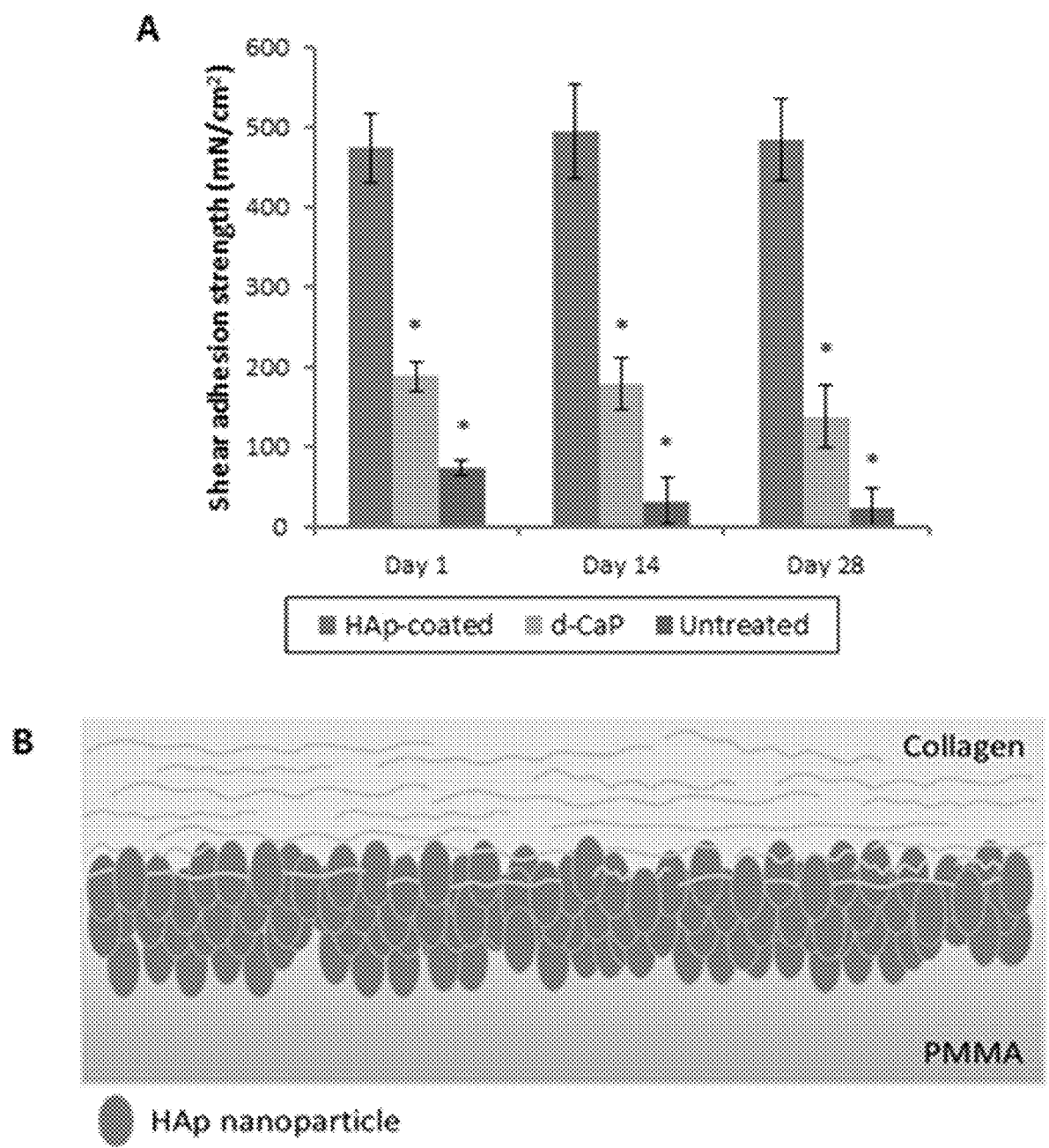
FIG. 10 shows a bar graph and a graphical illustration depicting interactions and shear bonding strength between collagen type I hydrogel and HAp-coated substrate.
Figure 11:
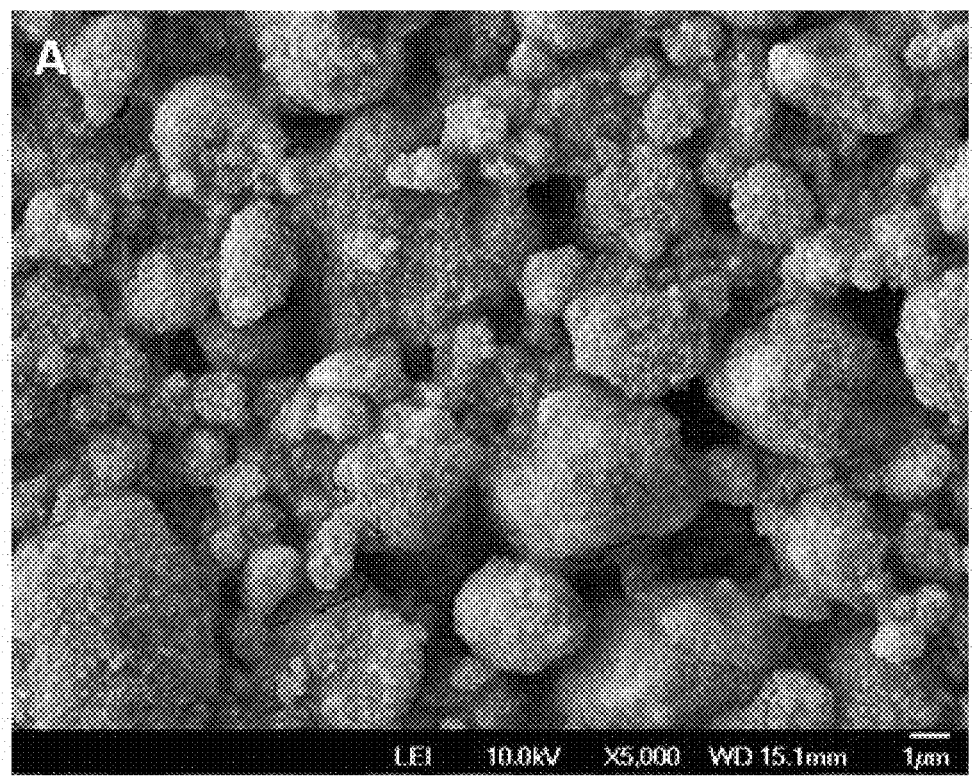
FIG. 11 shows a pair of Scanning Electron Microscopy (SEM) results depicting immobilization of $TiO_2$ nanoparticles on PMMA substrate.
Figure 11:
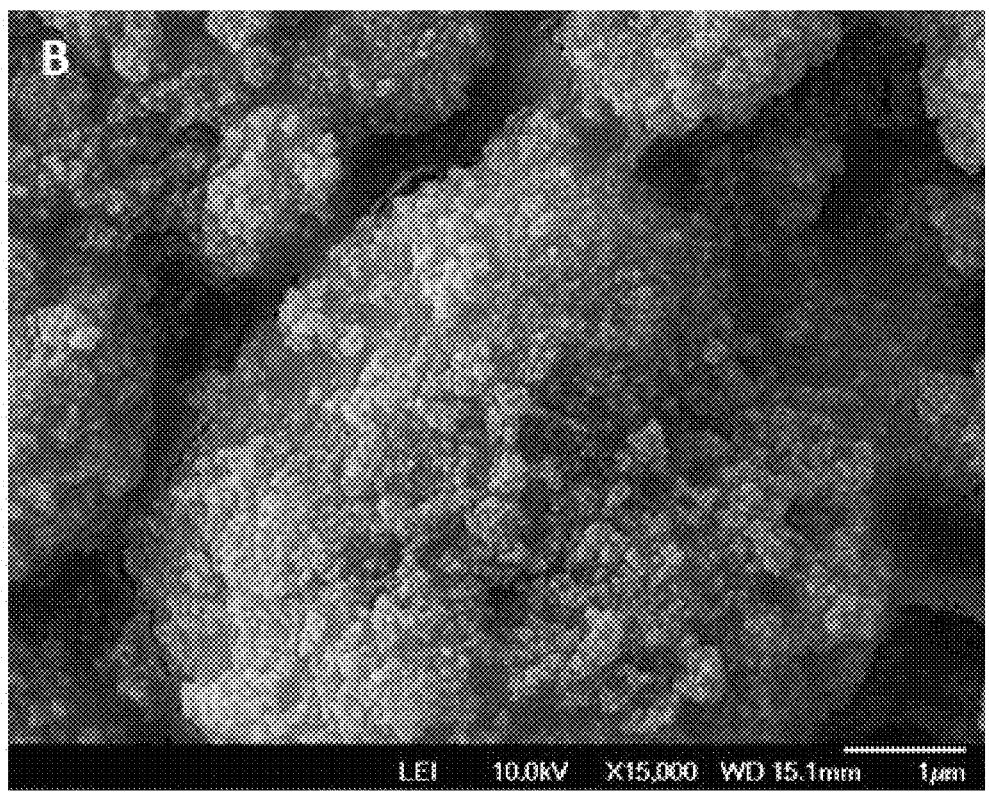

There was a marked improvement in the shear bond strength between collagen type I hydrogel on HAp-coated PMMA compared to the CaP-coated PMMA (coating method described in FIG. 2) and especially to the untreated PMMA group at all time points (p<0.001) (FIG. 10A). The shearing resistance remained stable over time on the HAp-coated surface (474±43 mN/cm² at day 1, 495±59 mN/cm² at day 14 and 485±51 mN/cm²). In contrast and consistent with the findings in the previous chapter, the shear adhesion strength of the hydrogel on d-CaP surface reduced over time from 190±18 mN/cm² at day 1 and 180±33 mN/cm² at day 14 to 138±39 mN/cm² at day 28. Besides the changes in surface chemistry, hydrophilicity and roughness of the PMMA surface, the enhanced adhesion could be attributed by the immobilized HAp that acted as an intermediate layer that interlocked the PMMA and collagen (FIG. 10B).

Using the same dipcoating technique, $TiO_2$ nanoparticles could also be immobilized on the PMMA substrate (FIGS. 8A and B). This shows that the dipcoating technique described here can be potentially applied for other types of bioceramic nanoparticles.

Exemplary Method 1

Following is an example of the step-by-step procedure of the nanoparticles dipcoating on a polymer sheet:

1. Dry the PMMA substrate in 37° C. overnight and in 60° C. for 1 hour before performing the dipcoating.

2. Mix 20% (w/v) HAp nanoparticles (needle shape; 60 nm in size) or $TiO_2$ nanoparticles (spherical shape; 50 nm in diameter) in 5% (w/v) PMMA (MW 120,000) in chloroform in a 30 ml bottle.

3. Stir the mixture for 1 minute before subjecting it to probe sonication.

4. Probe sonicate the mixture for 5 minutes to disperse the nanoparticles. Shake the mixture when the pulse is halted every 30 seconds. Probe sonication parameter is as follows:
   a. Probe size: Large
   b. Amplification level: 50%
   c. Stop pulse for 5 seconds every 30-second pulse.

5. Set up the dipcoater with the following basic parameters:
   a. Dipping and retraction speed: both 240 mm/min.
   b. Number of dipping required: 1.
   c. Length of dipcoating time: 60 seconds.

6. Place the mixture below the PMMA substrate and start the dipcoating procedure.

7. Leave the coated PMMA substrate for at least 30 minutes on the dipcoater after the completion of the dipcoating process to allow for complete evaporation of chloroform from the surface.

8. Wash the nanoparticles-coated substrate with 70% ethanol for 3 times 15 minutes each and rinse with copious amounts of distilled water.

9. Dry the substrate for overnight in 37° C. vacuum incubator.

10. The following day, treat the nanoparticles-immobilized substrate with oxygen plasma with the following parameters:
    a. Power: 200W
    b. Oxygen flow rate: 20 sccm
    c. Length of treatment: 30 seconds 11. Wash the plasma treated substrate with 70% ethanol for 3 times 15 minutes each and rinse with copious amounts of distilled water.

12. Dry the substrate in 37° C. vacuum incubator overnight.

Exemplary Method 2

The following is another example of a step-by-step procedure of the nanoparticles dipcoating process:

1. Cleaning of PMMA substrate.
   a. The substrate is first cleaned in 70% ethanol for 2 times 10 minutes in batch sonicator.
   b. Following sonication, the substrate is washed in deionized water ($dH_2O$) for 3 times 10 minutes.
   c. The substrate is dried in 60° C. incubator overnight and in 37° C. vacuum incubator until further use.

2. Preparation of dipcoating solution.
   a. 5% (w/v) PMMA (MW 120,000) is first dissolved in organic solvent, such as chloroform ($CHCl_3$), dichloromethane ($CH_2Cl_2$), acetone, toluene or tetrahydrofuran (THF).
   b. HAp or $TiO_2$ nanoparticles (needle or spherical shape; any size from 10 nm to 200 nm) with concentration from 5% (w/v) to 50% (w/v) are then added into the solution mixture prepared in step a above.
   c. The dipcoating solution (nanoparticles, PMMA and organic solvent) is vortexed for 1 minute before being subjected to probe sonication.
   d. The probe sonication with amplification level of 50% is performed for 5 minutes (5-second-pulse on and 5-second-pulse off cycles) to disperse the nanoparticles.
   e. Following probe sonication, the dipcoating solution is let to settle down for at least 1 minute and not more than 5 minutes before the next dipcoating step.

3. Dipcoating or immobilization of nanoparticles on the PMMA substrate is performed with an automated dipcoater. Dipcoating time can be varied from 5-120 seconds (the longer the dipcoating time, the thicker the HAp layers that form).

4. Leave the coated PMMA substrate for at least 30 minutes on the dipcoater after the completion of the dipcoating process to allow for complete evaporation of chloroform from the surface.

5. Wash the nanoparticles-coated substrate with 70% ethanol for 3 times 15 minutes each and rinse with copious amounts of distilled water.

6. Dry the substrate for overnight in 60° C. vacuum incubator.

7. After drying, the nanoparticles-immobilized substrate is treated with either oxygen or argon plasma for 2 minutes to remove contaminants that may have mask the nanoparticles during the earlier dipcoating process.

8. The plasma treated substrate is then washed with 70% ethanol for 2 times 10 minutes and with $dH_2O$ for 3 times 10 minutes.

9. The substrate is dried in 60° C. incubator overnight and in 37° C. vacuum incubator until further use.

REFERENCES

1. Whitcher, J. P.; Srinivasan, M.; Upadhyay, M. P. Corneal blindness: a global perspective. Bull. World Health Organ. 2001, 38, 1625-1631.

2. Pascolini, D.; Mariotti, S. P. Global estimates of visual impairment 2010. Br. J. Ophthalmol. 2012, 96, 614-618.

3. Tan, D. T.; Dart, J. K.; Holland, E. J.; Kinoshita, S. Corneal transplantation. Lancet 2012, 379, 1749-1761.

4. Childress, J. F. Ethical criteria for procuring and distributing organs for transplantation. J Health Polit. Policy Law 1989, 14, 87-113.

5. Muraine, M. C.; Collet, A.; Brasseur, G. Deep lamellar keratoplasty combined with cataract surgery. Arch. Ophthalmol. 2002, 120, 812-815.

6. Ilhan-Sarac, O.; Akpek, E. K. Current concepts and techniques in keratoprosthesis. Curr. Opin. Ophthalmol. 2005, 16, 246-250.

7. Gomaa, A.; Comyn, O.; Liu, C. Keratoprostheses in clinical practice—a review. Clin Exp Ophthalmol. 2010, 38, 211-224.

8. Nouri, M.; Terada, H.; Alfonso, E. C.; Foster, C. S.; Durand, M. L.; Dohlman, C. H. Endophthalmitis after keratoprosthesis: incidence, bacterial causes, and risk factors. Arch. Ophthalmol. 2001, 119, 484-489.

9. Garcia, J. P. Jr; de la Cruz, J.; Rosen, R. B.; Buxton, D. F. Imaging implanted keratoprostheses with anterior-segment optical coherence tomography and ultrasound biomicroscopy. Cornea 2008, 27, 180-188.

10. Riau, A. K.; Mondal, D.; Yam, G. H., Setiawan, M.; Liedberg, B.; Venkatraman, S. S.; et al. Surface modification of PMMA to improve adhesion to corneal substitutes in a synthetic core-skirt keratoprosthesis. ACS Appl. Mater. Interfaces 2015, 7, 21690-21702.

11. Wang, L.; Jeong, K. J.; Chiang, H. H.; Zurakowski, D.; Behlau, I.; Chodosh, J.; et al. Hydroxyapatite for keratoprosthesis biointegration. Invest. Ophthalmol. Vis. Sci. 2011, 52, 7392-7399.

12. Salvador-Culla, B.; Jeong, K. J.; Kolovou, P. E.; et al. Titanium coating of the Boston keratoprosthesis. Transl Vis Sci Technol. 2016, 5, 17

13. Turek S L. Physiology and mineralization of bone: In: Orthopeadics: principles and their applications. 4th ed. Philadelphia: J. B. Lippincott Company; 1984. p. 136-144.

14. Shapses, S. A.; Cifuentes, M.; Spevak, L.; et al. Osteopontin facilitates bone resorption, decreasing bone mineral crystallinity and content during calcium deficiency. Calcif Tissue Int. 2003, 73, 86-92.

15. Zheng, X.; Huang, M.; Ding, C. Bond strength of plasma-sprayed hydroxyapatite/Ti composite coatings. Biomaterials. 2000, 21, 841-849.

16. Stoch, A.; Brozek, A.; Kmita, G.; Stoch, J.; Jastrz, W. Electrophoretic coating of hydroxyapatite on titanium implants. J. Mol. Structure. 2001, 596, 191-200.

17. Nieh, T. G.; Jankowski, A. F.; Koike, J. Processing and characterization of hydroxyapatite coatings on titanium produced by magnetron sputtering. J. Mater. Res. 2001, 16, 3238-3245.

The invention claimed is:

1. A method of surface treatment of an optical cylinder of a corneal prosthesis, wherein the method comprises:
   a) contacting an optical cylinder comprising a solid polymer with a mixture comprising an organic solvent, a dispersant, and a plurality of nanoparticles to form a substantially uniform layer on a circumference of a solid polymer surface of the optical cylinder, and
   b) removing the organic solvent to immobilize the nanoparticles and the dispersant on the circumference of the solid polymer surface of the optical cylinder, thereby forming the optical cylinder of the corneal prosthesis, wherein the nanoparticles are hydroxyapatite (HAp) particles.

2. The method of claim 1, comprising contacting the optical cylinder with the mixture in a) by spray coating or dipcoating.

3. The method of claim 1, wherein a length of time for the contacting in a) is from 45 seconds to 75 seconds.

4. The method of claim 1, comprising removing the organic solvent in b) by evaporating or heating.

5. The method of claim 1, wherein a concentration of the nanoparticles in the mixture is from 15% (w/v) to 25% (w/v).

6. The method of claim 1, wherein a concentration of the dispersant in the mixture is from 4% (w/v) to 6% (w/v).

7. The method of claim 1, wherein the nanoparticles have a size of 50 nm to 200 nm.

8. The method of claim 1, wherein the nanoparticles have a size of about 60 nm.

* * * * *